US010207229B2

(12) United States Patent
Bruening et al.

(10) Patent No.: US 10,207,229 B2
(45) Date of Patent: Feb. 19, 2019

(54) FUNCTIONALIZATION OF A POROUS MEMBRANE WITH AN ADSORBED POLYACID

(71) Applicant: BOARD OF TRUSTEES OF MICHIGAN STATE UNIVERSITY, East Lansing, MI (US)

(72) Inventors: Merlin L. Bruening, East Lansing, MI (US); Gregory L. Baker, East Lansing, MI (US); Somnath Bhattacharjee, Durham, NC (US); Yiding Ma, Ann Arbor, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 15/251,628

(22) Filed: Aug. 30, 2016

(65) Prior Publication Data

US 2017/0050151 A1    Feb. 23, 2017

Related U.S. Application Data

(62) Division of application No. 13/799,380, filed on Mar. 13, 2013, now Pat. No. 9,459,188.

(Continued)

(51) Int. Cl.
*B01D 67/00* (2006.01)
*G01N 1/34* (2006.01)
(Continued)

(52) U.S. Cl.
CPC ..... *B01D 67/0088* (2013.01); *B01D 15/3828* (2013.01); *B01J 20/22* (2013.01);
(Continued)

(58) Field of Classification Search
CPC .................................................. B01D 67/0088
(Continued)

(56) References Cited

U.S. PATENT DOCUMENTS 6,402,918 B1    6/2002  Schlenoff et al.
2004/0211730 A1*  10/2004  Zhang ............... B01J 20/103
                                                        210/656

(Continued)

OTHER PUBLICATIONS

Bhattacharjee et al., Formation of high-capacity protein-adsorbing membranes through simple adsorption of poly(acrylic acid)-containing films at low pH, Langmuir, 28(17):6885-92 (2012).

(Continued)

*Primary Examiner* — Christine T Mui
*Assistant Examiner* — Emily R. Berkeley
(74) *Attorney, Agent, or Firm* — Marshall, Gerstein & Borun LLP

(57) ABSTRACT

The disclosure relates to a process and related article for functionalizing a porous membrane by contacting the membrane with a polyacid polymer at low pH to stably adsorb a polyacid layer on the membrane pore surface. The resulting functionalized membrane is characterized by a high density of free acid groups, resulting in a higher specific capacity for its intended application. The process allows functionalization of porous membranes in a very simple, one-step process. Such functional membranes may find multiple uses, including rapid, selective binding of proteins for their purification or immobilization.

34 Claims, 10 Drawing Sheets

Related U.S. Application Data

(60) Provisional application No. 61/611,704, filed on Mar. 16, 2012.

(51) Int. Cl.
  *B01J 20/28*      (2006.01)
  *B01D 15/38*     (2006.01)
  *B01J 47/12*     (2017.01)
  *B01J 20/32*     (2006.01)
  *B01J 20/22*     (2006.01)
  *C07K 1/22*      (2006.01)
  *G01N 33/543*    (2006.01)

(52) U.S. Cl.
  CPC ....... *B01J 20/28033* (2013.01); *B01J 20/327* (2013.01); *B01J 20/328* (2013.01); *B01J 20/3265* (2013.01); *B01J 47/12* (2013.01); *C07K 1/22* (2013.01); *G01N 1/34* (2013.01); *G01N 33/54306* (2013.01); *Y10T 428/249991* (2015.04); *Y10T 436/25375* (2015.01)

(58) Field of Classification Search
  USPC ........................................................ 436/177
  See application file for complete search history.

(56) References Cited

U.S. PATENT DOCUMENTS

| | | |
|---|---|---|
| 2005/0106663 A1 | 5/2005 | Braman et al. |
| 2008/0179188 A1 | 7/2008 | Nelson et al. |
| 2009/0313813 A1 | 12/2009 | Sato et al. |
| 2013/0244338 A1 | 9/2013 | Bruening et al. |

OTHER PUBLICATIONS

Bruening et al., Creation of functional membranes using polyelectrolyte multilayers and polymer brushes, Langmuir, 24(15):7663-73 (2008).

Bruening, Modified membranes for protein purification and analysis, University of Notre Dame presentation, 25 pp. (Mar. 8, 2012).

Bruening, Modified membranes for protein purification and analysis, University of Texas Presentation, 31 pp (Dec. 8, 2011).

Dotzauer et al., Catalytic membranes prepared using layer-by-layer adsorption of polyelectrolyte/metal nanoparticle films in porous supports, Nano. Lett., 6(10):2268-72 (2006).

Dotzauer et al., Nanoparticle-containing membranes for the catalytic reduction of nitroaromatic compounds, Langmuir, 25(3):1865-71 (2009).

Hautojavi et al., Characterization of graft-modified porous polymer membranes, Ind. Eng. Chem. Res., 35:450-7 (1996).

Jain et al., Protein purification with polymeric affinity membranes containing functionalized poly(acid) brushes, Biomacromolecules, 11(4):1019-26 (2010).

Liu et al., Ion-Exchange Membranes Prepared Using Layer-by-Layer Polyelectrolyte Deposition, J. Memb. Sci., 354(1-2):198-205 (2010).

Mermut et al., Structural and Mechanical Properties of Polyelectrolyte Multilayer Films Studied by AFM, Macromolecules, 36(23):8819-24 (2003).

Shiratori et al., pH-dependent thickness behavior of sequentially adsorbed layers of weak polyelectrolytes, Macromolecules, 33:4213-9 (2000).

* cited by examiner

FUNCTIONALIZATION OF A POROUS MEMBRANE WITH AN ADSORBED POLYACID

CROSS REFERENCE TO RELATED APPLICATIONS

This application is a divisional of U.S. patent application Ser. No. 13/799,380 filed Mar. 13, 2013, which in turn claims priority to U.S. Provisional Application No. 61/611,704 (filed on Mar. 16, 2012), both of which are incorporated herein by reference in their entireties.

STATEMENT OF GOVERNMENT INTEREST

This invention was made with government support under GM080511 awarded by the National Institutes of Health. The government has certain rights in the invention.

BACKGROUND OF THE DISCLOSURE

Field of the Disclosure

The disclosure relates to a process and related article for functionalizing a porous membrane by contacting the membrane with a polyacid polymer at low pH to stably adsorb a polyacid layer on the membrane pore surface. The process allows functionalization of porous membranes in a very simple, one-step process. Such functional membranes may find multiple uses, including rapid, selective binding of proteins for their purification or immobilization.

Brief Description of Related Technology

Affinity adsorption of tagged recombinant proteins is a vital step in their purification. Remarkably, specific binding of the tagged protein to ligands immobilized in packed columns often leads to eluted protein purities >90%. However, slow diffusion of large macromolecules into the affinity resin sometimes results in long separation times that are particularly deleterious for purification of sensitive proteins or their complexes. In large scale affinity adsorption, column packing is also challenging, and high pressure drops may occur.

SUMMARY

The disclosure relates to a process and corresponding article for functionalizing a porous membrane by contacting the membrane with a polyacid polymer at low pH (e.g., generally less than 4) to stably adsorb a polyacid layer on the surfaces of the membrane pores. As illustrated in the examples, it was unexpectedly found that a polyacid polymer with pendent free acid groups (e.g., poly(acrylic acid) (PAA)) could be stably and directly adsorbed on a membrane surface. It was previously thought that an intermediate adhesion layer having both a high hydrophobic character and available ionic groups (e.g., poly(styrene sulfonate) (PSS) having hydrophobic aromatic rings and ionic sulfonate groups) was required to adhere to the membrane material and provide a basis for the layer-by-layer growth/adsorption of other polymeric layers having desired functionalities. It was further thought that higher pH values (e.g., generally at or above the isoelectric point of a given polymer to be adsorbed) were required to form a well-adhered, stable polymeric film (e.g., at a pH value above 4 to 4.5 as an approximate isoelectric point for PAA). As shown in the application examples, however, it was found that polyacid polymers could be stably adsorbed at low pH values, and further that no adhesion layers were necessary. Further, the membrane-adsorbed polyacid polymers were found to have a high density of free acid groups, which could be used directly as functional groups for an ion-exchange process or which could be further derivatized for any desired application (e.g., selective binding of proteins for purification or immobilization). Thus, the disclosed process and resulting article exhibit a synergy in that the low pH-process provides both (i) a favorable adhesion process for the polyacid polymer (e.g., resulting in a structurally stable functionalized membrane article) and (ii) an increased density of free acid groups (e.g., resulting in a functionalized membrane with a higher specific capacity/activity for its intended application).

In one aspect, the disclosure relates to a method for functionalizing a porous membrane, the method comprising: (a) providing a porous membrane substrate comprising a plurality of membrane pores; and (b) contacting the membrane pores with an aqueous fluid mixture (i) having a pH value less than 3.8 and (ii) comprising a polyacid polymer comprising (pendent) free acid groups selected from the group consisting of carboxylic acid groups (—COOH), carboxylate groups (—COO$^-$), and combinations thereof for a time sufficient to (stably) adsorb a polyacid layer on surfaces of the membrane pores, thereby forming a polyacid-coated porous membrane comprising the free acid groups. Alternatively or additionally, the pH value of the aqueous fluid mixture can be at least 0.2, 0.4, 0.6, or 0.8 pH units less than the isoelectric point of the polyacid polymer. The free acid groups generally are not paired to another group (e.g., such as when a carboxylic acid group is covalently bound to another functional group via a reaction product such as amide or ester, or such as when a carboxylate group is ionically paired to a cation such as in an adjacent polycation layer).

Various refinements and extensions of the functionalization method and resulting functionalized membrane are possible.

For example, the plurality of membrane pores can have an average pore size of at least 0.02 µm, 0.1 µm, 0.2 µm, 0.5 µm, 1 µm, or 2 µm and/or up to 3 µm, 4 µm, 5 µm, 6 µm, 8 µm, 10 µm, 20 µm, or 50 µm. The foregoing sizes/ranges can additionally or alternatively represent bounds of a pore size distribution in the membrane. A size range of about 0.5 µm to about 10 µm is suitable, for example, for protein isolation applications, in particular when the sample containing the protein to be isolated/purified is admixed with other larger, non-target interfering components such as cell lysate products. Lower pore sizes down to about 0.1 µm can be used for samples without larger interfering matter such as for isolation of (small) proteins without cell lysate products and/or isolation of metal ions (e.g., generally with the free acid group or with some metal-specific ligand based on further derivation, such as to capture a Cu$^{2+}$ byproduct of a click chemistry reaction system). Other pore sizes (e.g., up to about 50 µm) can be used to target other analytes, for example including oligonucleotides/DNA and/or microorganisms such as bacteria, viruses, and/or characteristic oligonucleotides/DNA thereof (e.g., using an analyte-complementary antibody or probe oligonucleotide/DNA immobilized via derivatization of the polyacid free acid groups to provide a membrane functionalized with a capture probe/analyte binding pair member).

In various embodiments, the porous membrane substrate can comprise a synthetic polymeric membrane material selected from the group consisting of cellulose acetates, nitrocelluloses, cellulose esters, polysulfones, polyether sulfones, polyacrylonitriles, polyamides (nylons), polyimides, polyethylenes, polypropylenes, polytetrafluoroethylenes, polyvinylidene fluorides, polyvinylchlorides, hydroxylated derivatives of the foregoing, and combinations thereof. Hydroxyl group-containing materials (e.g., which can be present in the native form of the polymeric membrane material or as a hydroxylated derivative of the polymeric membrane material) can be useful to promote hydrogen bonding interactions with the polyacid. Such hydroxyl functionality is not required however, since hydrophobic interactions (among others) between the membrane material and the polyacid backbone can provide substantial adhesion forces as well.

In an embodiment, at least 50%, 60%, 70%, 80%, 90%, or 95% of the polyacid free acid groups in the aqueous fluid mixture are in the form of carboxylic acid groups (—COOH). Alternatively or additionally, at least some of the free acid groups can be in carboxylate form (—COO$^-$), such as at least 5%, 10%, or 20% and/or up to 10%, 20%, 30%, 40%, or 50%. At least some carboxylate groups can be desirable in multi-layer films so that the polyacid layer has some ionic groups to promote interlayer adhesion with neighboring polycation layers. Conversely, in membranes functionalized with only a monolayer of polyacid, the polyacid can have any desired level of carboxylic groups and exhibit good adhesion properties, for example where all or substantially all free acid groups are in the form of carboxylic acid groups. The foregoing values for carboxylic acid and carboxylate content apply to the free acid groups of the polyacid layer as deposited on the membrane as well, although they need not be identical to those of the original polyacid polymer in the aqueous fluid mixture prior to deposition.

As noted above, the polyacid-coated porous membrane deposited according to the disclosed methods has a substantially higher free acid group content relative to equivalent polyacid layers deposited at higher pH values. For example, the polyacid-coated porous membrane can have a free acid group content of at least 1.25, 1.5, 1.75, 2, 2.5, 3, or 4 and/or up 3, 4, 5, 6, 8, or 10 times that of an analogous polyacid-coated porous membrane in which the aqueous fluid mixture containing the polyacid to be deposited had a higher reference pH value such as 4 or 5. This relative free acid group content can be determined/approximated, for example, by measuring a chemical moiety such as a ligand-bound metal (e.g., NTA-complexed $Cu^{2+}$ or $Ni^{2+}$) that corresponds to the free acid group content of the as-deposited polyacid. In this example, the metal-binding ligand selectively binds to the free acid groups during derivatization/attachment to provide a measurable correlation to the free acid group content of the polyacid layer as initially deposited (e.g., by measuring the metal-binding capacity of the derivatized coated membrane). The metal ion may also bind to the free carboxylic acid groups (e.g., underivatized groups) in the film.

In the functionalized membrane, the polyacid layer can be stably adsorbed on the surfaces of the membrane pores due to various interactions, such as one or more of hydrophobic interactions, hydrogen bonding interactions, and coordination interactions. In an embodiment, the polyacid-membrane adhesion forces are free or substantially free of covalent substrate attachments (e.g., such as when the polyacid is adsorbed directly on the substrate). In another embodiment, the polyacid-membrane adhesion forces are free or substantially free of ionic attachment forces to the substrate. In other instances, however, ionic forces may be present, such as when the polyacid is adsorbed on an intervening polycation layer or when the membrane material has ionic functional groups. The adsorbed polyacid layer is resistant to high-pH treatment such as a rinse with sodium hydroxide or other strong base for membrane decontamination and re-use (e.g., allowing the membrane to be treated/decontaminated without removing or otherwise substantially degrading the adsorbed (functionalized) polyacid layer). After the basic rinse, the membrane can be rinsed/reconditioned with DI water and/or a suitable sample buffer (e.g., such as a buffer for sample delivery or target analyte elution).

The specific polyacid polymer used is not particularly limited, but it suitably comprises repeating units having one or more pendent free acid groups. In many embodiments, the polyacid polymer has an ethylenic backbone. For example, the polyacid polymer can include mono-acid repeating units (e.g., acrylic acid and methacrylic acid repeating units) and/or poly-acid repeating units (e.g., itaconic acid and maleic acid as examples of di-acids) either in a homopolymer or copolymer. Suitable homopolymers can include poly(acrylic acid) (PAA) and poly(methacrylic acid). Suitable copolymers can include other acid-containing repeating units or other non-acid-containing units (e.g., alkylene-derived repeating units such as ethylene, propylene, etc.). In an embodiment, a monomer of the polyacid repeating unit can be represented by $R_1R_2C\!=\!CR_3R_4$, where $R_1$-$R_4$ are independently selected from H and carbon-containing groups having from 1 or 2 to 4, 6, or 8 carbons (e.g., a hydrocarbon group such as an alkyl group), potentially in addition to one or more N, O, S heteroatoms. At least one of $R_1$-$R_4$ is a carbon-containing group having one or more free acid groups (e.g., $R_1$-$R_3$ are H and $R_4$ is —COOH or —COO$^-$ for acrylic acid/acrylate; $R_1$-$R_2$ are H, $R_3$ is $CH_3$, and $R_4$ is —COOH or —COO$^-$ for methacrylic acid/methacrylate).

In a refinement, the polyacid polymer can comprise repeating units that comprise a metal-binding ligand group. In various embodiments, the metal-binding ligand group can itself include the free acid group(s) of the polyacid, or the free acid groups can be separate from the metal-binding portion of the polyacid polymer. Suitably, the metal-binding ligand group contains at least one (e.g., 1, 2, 3, 4, or more than 4) nitrogen atom and/or at least one (e.g., 1, 2, 3, 4, or more than 4) free acid group such as an acetic acid group to provide a polydentate metal-binding group. In an embodiment, a monomer of the polyacid repeating unit can be represented by $R_1NR_2R_3$. $R_1$ is a carbon-containing group having from 2 or 4 to 4, 6, 8, 10, or 12 carbons (e.g., a hydrocarbon group such as an alkylene or aromatic group), potentially in addition to one or more N, O, S heteroatoms that contains at least one ethylenic unsaturation for polymerization. $R_2$ and $R_3$ are independently selected from H or carbon-containing groups having from 1 or 2 to 4, 6, or 8 carbons (e.g., a hydrocarbon group such as an alkyl group), potentially in addition to one or more N, O, S heteroatoms, where at least one of $R_2$ and $R_3$ is a carbon-containing group having one or more free acid groups (e.g., at least one of $R_2$ and $R_3$ is or contains a —COOH or —COO$^-$ group). In one refinement of this embodiment, $R_1$ is $H_2C\!=\!CH$—$CH_2$—, and $R_2$ and $R_3$ are —$CH_2COOH$ to provide a polymerizable tridentate metal-binding iminodiacetic group (e.g., a polyacid polymer including a N-(2-propenyl) iminodiacetic acid monomer unit). In another refinement of this embodiment, $R_1$ is $H_2C\!=\!CH$—$C(COOH)H$—, and $R_2$ and $R_3$ are —$CH_2COOH$ to provide a polymerizable tetradentate metal-binding nitrilotriacetic group analogous to that of aminobutyl NTA (e.g., a polyacid polymer including a N-(1-carboxy-2-propenyl) iminodiacetic acid monomer unit). The polyacid polymers which themselves include the metal-binding ligand group can be homopolymers of the given repeating unit or they can be copolymers with other repeating units (e.g., acrylic acid or otherwise).

A variety of conditions may be used to deposit/adsorb the polyacid from the aqueous fluid medium onto the porous membrane. For example, the pH value of the aqueous fluid mixture can be at least 1, 1.5, or 2 and/or up to 2, 2.5, 3, 3.2, or 3.5 (e.g., depending on the particular polyacid and/or to control the relative distribution of free acid groups between the carboxylic acid form and the carboxylate form). Alternatively or additionally, the deposition pH can be specified relative to the isoelectric point of the polyacid such that the pH of the aqueous fluid mixture is at least 0.2, 0.5, 0.8, 1, 1.5, 2, or 2.5 and/or up to 2, 2.5, 3, or 3.5 units less than the isoelectric point of the polyacid polymer. Suitably, the aqueous fluid mixture is in the form of an aqueous solution comprising the polyacid polymer and further comprising an electrolyte (e.g., an inorganic salt) in solution.

The polyacid layer can be adsorbed onto the porous membrane surfaces in various structural embodiments. For example, the polyacid layer can be adsorbed directly on the porous membrane substrate (e.g., no adhesion layer such as poly(styrene sulfonate) (PSS) or other polyelectrolyte is required as an intermediate between the membrane substrate and the polyacid). In an alternative embodiment, the polyacid layer is immobilized on the porous membrane substrate via one or more adhesion layers, wherein at least one of the adhesion layers is adsorbed directly on the porous membrane substrate (e.g., an adhesion layer such as poly(styrene sulfonate) or other polyelectrolyte such as in the PSS/PAH/PAA embodiment illustrated in the examples). In another embodiment, the polyacid-coated porous membrane has a monolayer of the polyacid polymer adsorbed directly on the porous membrane substrate and comprising the free acid groups (e.g., the single-PAA embodiment adsorbed directly on the polymeric membrane surface and illustrated in the examples). In another embodiment, the polyacid-coated porous membrane substrate comprises a plurality of polyacid layers, wherein (i) a first polyacid layer is adsorbed directly on the porous membrane substrate and (ii) one or more further polyacid layers are adhered to adjacent polyacid layers via one or more intervening polycation layers (e.g., polyethyleneimine (PEI) or poly(allyl amine) (PAH) such as in the PAA/PAH/PAA and PAA/PEI/PAA embodiments illustrated in the examples). Such multilayer structures can be formed by performing a layer-by-layer polyelectrolyte adsorption process to deposit alternate layers of (i) the polyacid at a pH value less than 3.8 and (ii) the polycation. The polycation layers are suitably deposited at the same or similar pH value as that of the polyacid layers, but higher pH values above 3.8 or 4 can be used). While a higher pH deposition of the polycation could decrease the amount of free acid groups in the bulk/interior of the film, the outermost polyacid layer will exhibit the desired high free acid group level as a result of having been deposited under the low-pH conditions in the final layer-by-layer deposition step. In any of the foregoing embodiments, the low-pH adsorption of the polyacid still results in a high density of free acid groups in the membrane.

In an extension, the method for functionalizing a porous membrane can further comprise: (c) derivatizing the free acid groups of the polyacid-coated porous membrane to (covalently) attach other functional groups such as protein affinity tag-binding ligands thereto at surfaces exposed to membrane pore void volumes. In various embodiments, the protein affinity tag-binding ligands are selected from the group consisting of polyhistidine tag-binding ligands (e.g., metallic ions such as $Ni^{2+}$ or $Cu^{2+}$ which are in turn immobilized in a suitable metal-ligand complex), glutathione, glutathione-S-transferase (GST) tag-binding derivatives thereof, amylose, maltose binding protein (MBP) tag-binding derivatives thereof, chitin, and chitin binding protein (CBP) tag-binding derivatives thereof. Suitable derivatives of the MBP and CBP tag-binding ligands can represent the inclusion of a linking group for covalent attachment of the affinity tag-binding ligand to the free acid groups as well as a potential non-polymeric form of amylose/chitin with sufficient α(1-4) bound glucose or N-acetylglucosamine residues for specific binding to an MBP tag or CBP tag, respectively.

In a refinement, derivatization of the free acid groups can comprise: (c-1) derivatizing the free acid groups of the polyacid-coated porous membrane to (covalently) attach metal-binding ligands thereto at surfaces exposed to membrane pore void volumes; and (c-2) contacting the metal-binding ligands with metallic ions to form (stable) metal-ligand complexes at the surfaces exposed to membrane pore void volumes (e.g., where the bound metals in turn serve as binding ligands for a protein affinity tag such as a polyhistidine tag). In various embodiments, the metallic ions comprise one or more of $Ni^{2+}$, $Cu^{2+}$, $Co^{2+}$, $Fe^{3+}$, and $Ga^{3+}$. In another embodiment, the metal-binding ligands can comprise one or more of nitrilotriacetic acid groups (e.g., aminobutyl NTA that has been amide-linked to free acid groups of the polyacid), iminodiacetic acid groups, and salts thereof (e.g., including carboxylate forms thereof).

In another aspect, the disclosure relates to a polyacid-coated porous membrane as generally formed according to the disclosed method in any of its various embodiments (e.g., including the polyacid as deposited or after further derivatization to include binding ligands such as protein affinity tag-binding ligands, either with or without a bound affinity tagged-protein).

In an embodiment, the polyacid-coated porous membrane comprises: (a) a porous membrane substrate comprising a plurality of membrane pores; and (b) a polyacid layer adsorbed on surfaces of the membrane pores, the polyacid layer comprising a polyacid polymer comprising (pendent) free acid groups selected from the group consisting of carboxylic acid groups, carboxylate groups, and combinations thereof; wherein the polyacid layer is stably adsorbed on the surfaces of the membrane pores and is substantially free of covalent attachments to the surfaces of the membrane pores. The polyacid-functionalized porous membrane is suitably free or substantially free of covalent bonds formed between the polyacid and the polymeric material of the porous membrane substrate (e.g., having been formed in the absence of conditions intended to create covalent attachments to the substrate although some incidental linking reactions could occur in principle). In a refinement, the polyacid layer is stably adsorbed on the surfaces of the membrane pores due to one or more of hydrophobic interactions, hydrogen bonding interactions, and coordination interactions.

In another aspect, the disclosure relates to a method for binding a positively charged target analyte, the method comprising: (a) providing the polyacid-coated porous membrane formed according to any of the variously disclosed embodiments (e.g., including free acid groups but without necessarily having been further derivatized/functionalized with a target-specific capture ligand); (b) providing a feed fluid sample comprising a positively charged target analyte; (c) passing the feed fluid sample through the polyacid-coated porous membrane, thereby (i) binding at least some of the target analyte with the free acid groups and (ii)

providing a permeate fluid with at least some of the target analyte removed; and optionally (d) eluting the bound target analyte from the polyacid-coated porous membrane, thereby forming a purified permeate fluid comprising the target analyte. In a refinement, (i) the feed fluid sample further comprises non-positively charged non-target analytes and (ii) the purified permeate fluid is substantially free from the non-target analytes.

In another aspect, the disclosure relates to a method for binding an affinity-tagged target protein, the method comprising: (a) providing the polyacid-coated porous membrane formed according to any of the variously disclosed embodiments and including a protein affinity tag-binding ligand; (b) providing a feed fluid sample comprising a target protein comprising an affinity tag; (c) passing the feed fluid sample through the polyacid-coated porous membrane, thereby (i) binding at least some of the target protein via the affinity tag with the immobilized protein affinity tag-binding ligands and (ii) providing a permeate fluid with at least some of the target protein removed; and optionally (d) eluting the bound target protein from the polyacid-coated porous membrane, thereby forming a purified permeate comprising the target protein. In a refinement, (i) the feed fluid sample further comprises non-target proteins and (ii) the purified permeate is substantially free from the non-target proteins (e.g., non-target proteins without an affinity tag in general or without the affinity tag appropriate for the specific membrane).

Various embodiments for the protein affinity tag-binding ligand are possible. In one embodiment, (i) the affinity tag is a polyhistidine tag and (ii) the protein affinity tag-binding ligands comprise one or more of $Ni^{2+}$-ligand complexes and $Co^{2+}$-ligand complexes. In another embodiment, (i) the affinity tag is a glutathione-S-transferase (GST) tag and (ii) the protein affinity tag-binding ligands are selected from the group consisting of glutathione, glutathione-S-transferase (GST) tag-binding derivatives thereof, and combinations thereof. In another embodiment, (i) the affinity tag is a maltose binding protein (MBP) tag and (ii) the protein affinity tag-binding ligands are selected from the group consisting of amylose, maltose binding protein (MBP) tag-binding derivatives thereof, and combinations thereof. In another embodiment, (i) the affinity tag is chitin binding protein (CBP) tag and (ii) the protein affinity tag-binding ligands are selected from the group consisting of chitin, chitin binding protein (CBP) tag-binding derivatives thereof, and combinations thereof.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1A:
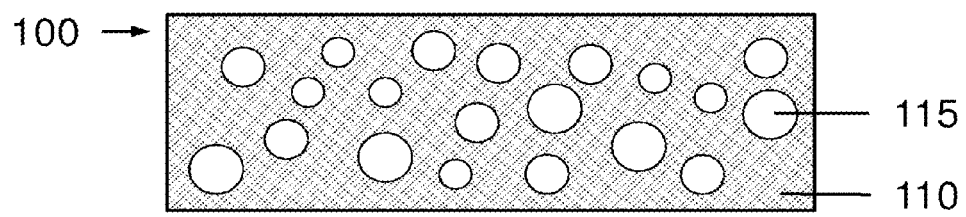
FIG. 1A illustrates a porous membrane substrate for functionalization according to the disclosure.

While the disclosed processes, compositions, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

Typical membrane modification includes polymerization from the surface. This is a relatively complex process, and often includes initiator attachment to the membrane. The current approach involves adsorption of a polyacid to the membrane. Hydrophobic interactions strongly attach the polymer to the surface. Although others have modified membranes through polymer adsorption, a feature of the disclosed process is adsorption at low pH to maintain a low fraction of ionized groups and promote the formation of highly swollen films after deprotonation of the acid groups. These highly swollen films rapidly bind large amounts of protein and can be further functionalized. The method is much more convenient than previous approaches to membrane modification. Protein binding capacities are higher than for commercial membranes.

The process involves simple passage of a polyacid solution through a membrane at low pH. Additional layers may be deposited by sequentially adsorbing polycations along with the polyanion at low pH. Subsequent binding at neutral pH leads to a high density of ion-exchange sites for protein binding. Derivatization of the acid groups with ligands such as $Ni^{2+}$ complexes allows selective binding of tagged proteins such as those containing polyhistidine.

FIGS. 1A-1E illustrate several membranes and related methods according to the disclosure. FIG. 1A illustrates a generalized porous membrane 100 (e.g., pre-functionalization or post-functionalization as described below, with or without a bound analyte) having a body/substrate 110 defining a plurality of pores 115 through which fluids may pass through the membrane 100. As noted above, suitable materials for the substrate 110 and the sizes for the pores 115 are not particularly limited and can be selected based on an intended use (e.g., chemical compatibility with polymeric layers to be adsorbed thereon, size compatibility with target materials/analytes passing through the membrane).

Figure 1B:
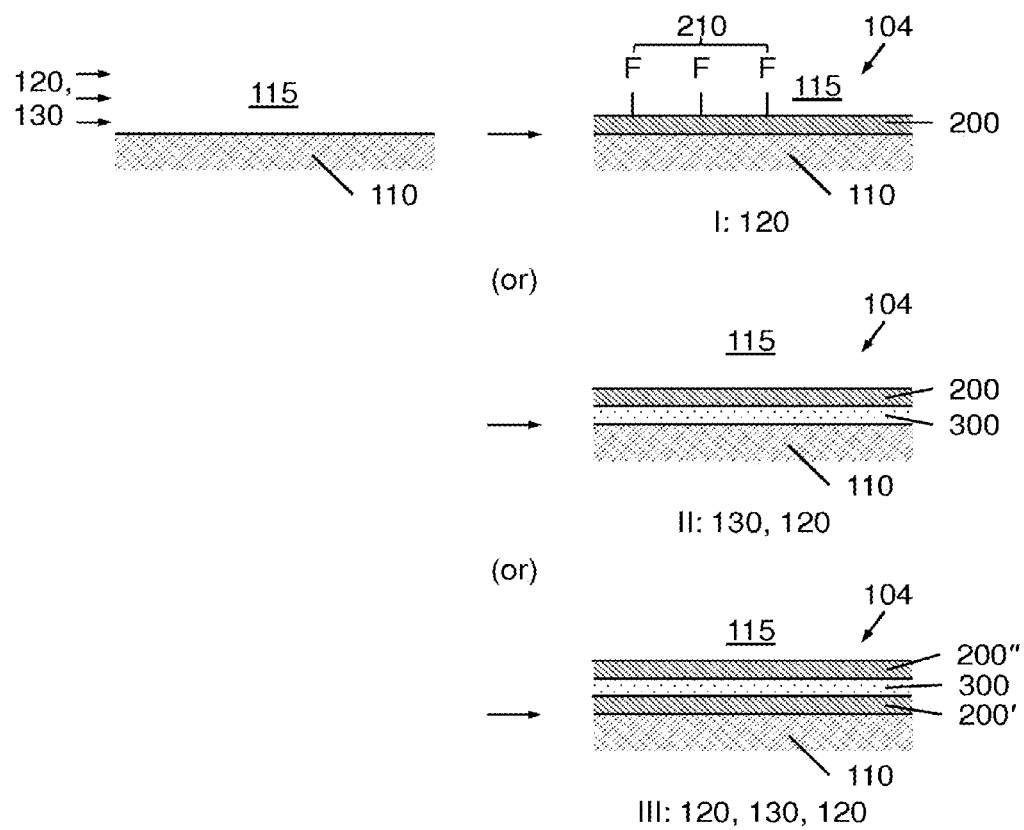
FIGS. 1B-1C illustrate functionalized membranes according to the disclosure, including functionalized membranes with free acid groups (FIG. 1B) and derivatized free acid groups (FIG. 1C).

FIG. 1B illustrates several methods for functionalizing a porous membrane 100. In general, the substrate 110 is contacted by passing fluid mixtures 120 and/or 130 through the pores 115. The mixture 120 can represent an aqueous fluid mixture including a polyacid polymer and having a low pH value suitable for forming a high-capacity adsorbed polyacid layer 200 with pendent free acid groups (F) 210. The mixture 130 can represent an aqueous fluid mixture including a polyelectrolyte (e.g., an adhesion promoter such as a polycation; generally other than a polyacid or polyanion) for forming an intermediate polyelectrolyte (or adhesion) layer 300 between neighboring substrate 110/polyacid 200 layers and/or neighboring polyacid 200'/polyacid 200" layers. The left side of FIG. 1B represents an unmodified membrane 100 prior to being treated/functionalized with one or more of the fluid mixtures 120, 130. The right side of FIG. 1B represents various functionalized porous membranes 104 including free acid groups 210 resulting from different functionalization methods. Embodiment I of FIG. 1B illustrates a single-step modification in which the membrane 100 is contacted with the low-pH polyacid mixture 120 to form a functionalized membrane 104 with a single polyacid layer 200 adsorbed directly on the substrate 110 surface. Embodiment II illustrates a two-step (e.g., sequential, layer-by-layer process) modification in which the membrane 100 is contacted with the polyelectrolyte mixture 130 followed by the polyacid mixture 120 to form a functionalized membrane 104 with a single polyacid layer 200 adsorbed/immobilized on the substrate 110 via an intermediate adhesion layer 300 surface adsorbed directly on the substrate 110 surface. Embodiment III illustrates a three-step (e.g., sequential, layer-by-layer process) process in which the membrane 100 is contacted with the polyacid/polycation mixtures 120/130/120 to form a functionalized membrane 104 with two polyacid layers 200'/200" adsorbed/immobilized on the substrate 110 with an intermediate polycation layer 300 therebetween. Although only specifically illustrated in Embodiment I, each of the illustrated polyacid layers 200/200'/200" include a high density of free acid groups 210 suitable for use as-is (e.g., to capture a positively charged analyte) or for further modification (e.g., derivatization to contain some other chemical functional group, such as a protein affinity tag-binding ligand).

Figure 1C:
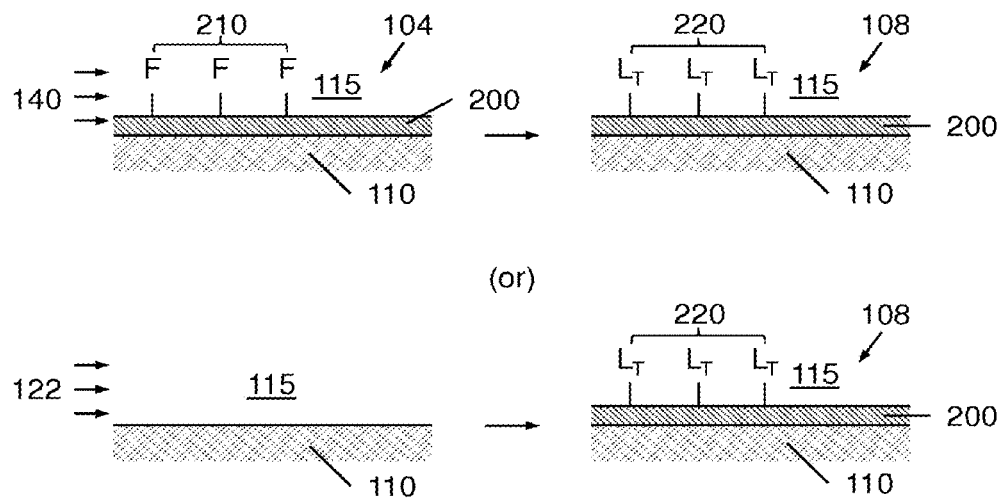

FIG. 1C illustrates additional methods for functionalizing a porous membrane 100, for example to form a functionalized membrane 108 including protein affinity tag-binding ligands ($L_T$) 220 (e.g., instead of or in addition to the free acid groups 210 as in the functionalized membrane 104). In the top embodiment of FIG. 1C, a previously functionalized membrane 104 can be further functionalized by contacting the membrane 104 with one or more derivatization components 140 (e.g., as mixtures in aqueous or non-aqueous (such as organic solvent-based) media). In addition to the chemical moiety/moieties forming the ligands 220, the components can further include one or more constituents as generally known in the art to mediate the derivatization/covalent attachment of the ligands 220 to the free acid groups 210 (e.g., converting some or all of the free acid groups 210 to the ligands 220, where some free acid groups 210 may remain in the functionalized membrane 108). For example, as described above and as illustrated in the examples, a metal-binding ligand (not separately shown) with amino functionality (e.g., ω-aminoalkyl nitrilotriacetic acid or iminodiacetic acid) can be covalently attached via amide linkages to the (former) free acid groups using N-(3-dimethylaminopropyl)-N'-ethylcarbodiimide hydrochloride (EDC), and N-hydroxysuccinimide (NHS). The metal-binding ligand can then be contacted with metallic ions (e.g., $Ni^{2+}$) to form a stable metal-ligand complex exposed to the membrane pore 115 volume and capable of serving as the protein affinity tag-binding ligands 220. In the bottom embodiment of FIG. 1C, a membrane 100 (e.g., which need not be previously functionalized) can be functionalized in a single step by contacting the substrate 110 with an aqueous fluid mixture 122 including a polyacid polymer itself containing metal-binding ligand groups and having a low pH value suitable for forming a high-capacity adsorbed polyacid layer 200 with pendent metal-binding ligand groups or protein affinity tag-binding ligand groups 220 (e.g., after further contact with metallic ions to form the metal-ligand complex with tag-binding affinity).

Figure 1D:
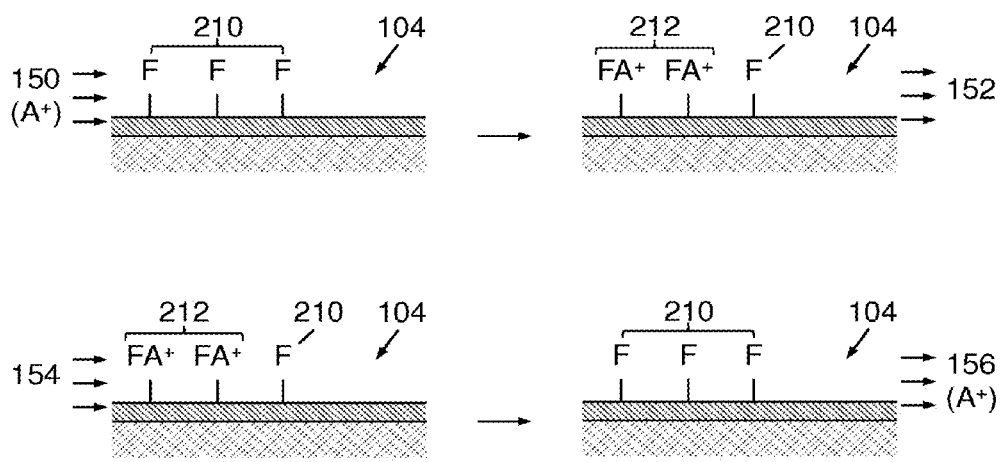
FIGS. 1D-1E illustrate methods of binding and recovering analytes from a sample using functionalized membranes according to the disclosure, including positively charged analytes (FIG. 1D) and protein analytes (FIG. 1E).

FIG. 1D illustrates a method of binding, capturing, and/or recovering an analyte from a fluid sample, for example a positively charged analyte such as a metallic ion or a polyatomic cation (e.g., whether metal-containing or otherwise). As shown in FIG. 1D, a feed fluid 150 containing or suspected of containing a positively charged analyte ($A^+$) is fed through the functionalized membrane 104. While not particularly limited, suitable positively charged analytes can include metals in various positive oxidation states (e.g., Al, Sb, As, Ba, Be, Cd, Ca, Cr, Co, Cu, Fe, Pb, Li, Mg, Mo, Mn, Ni, K, Se, Ag, Na, Sr, Sn, Ti, Tl, V, Zn, such as might be present in a water/wastewater stream to be purified). As the feed fluid 150 passes through the membrane 104, the free acid groups 210 can bind at least some of the analyte $A^+$, thus forming some at least some analyte-bound free acid groups ($FA^+$) 212 (e.g., where some unbound free acid groups 210 also can remain). The feed fluid 150 is removed from the membrane 104 as a permeate fluid 152 in which at least some of the analyte $A^+$ has been removed from the feed 150 (e.g., complete or substantially complete removal of the analyte $A^+$ provided that the membrane 104 binding capacity is not exceeded). Optionally, the analyte $A^+$ can be recovered/removed from the membrane 104 (e.g., when the analyte $A^+$ has value as a product or to regenerate the membrane 104 for further use). An elution/wash fluid 154 is fed to the membrane, removing at least some (or all) of the analyte $A^+$ from the analyte-bound free acid groups ($FA^+$) 212 to provide an eluate/purified permeate fluid 156 including the positively charged analyte ($A^+$).

Figure 1E:
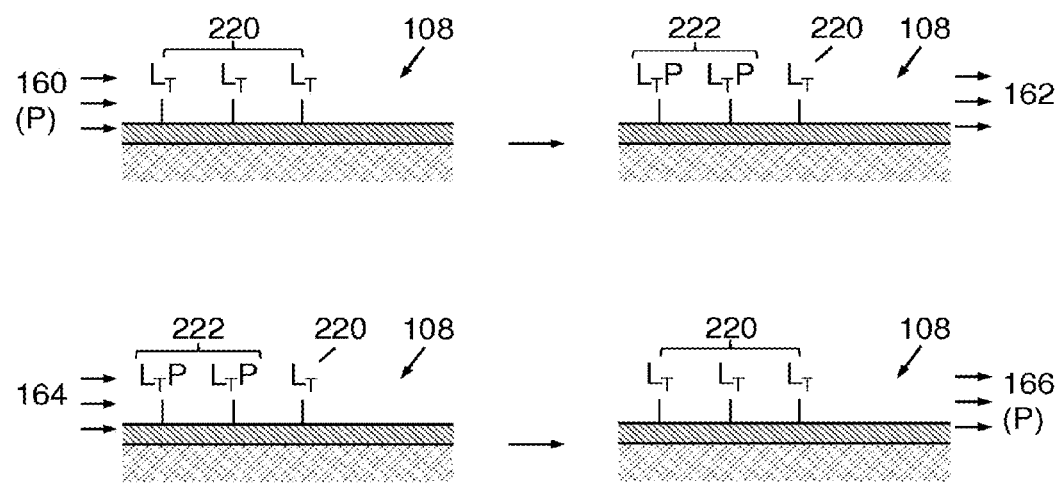

Similar to FIG. 1D, FIG. 1E illustrates a method of binding, capturing, and/or recovering an affinity-tagged target protein analyte from a fluid sample. As shown in FIG. 1E, a feed fluid 160 containing or suspected of containing an affinity-tagged target protein analyte (P) is fed through the functionalized membrane 108. While not particularly limited, suitable affinity tags include polyhistidine (His) tags, glutathione-S-transferase (GST) tags, maltose binding protein (MBP) tags, and chitin binding protein (CBP) tags. As the feed fluid 160 passes through the membrane 108, the affinity tag-binding ligands 220 can bind at least some of the protein analyte P, thus forming some at least some analyte-bound ligand groups ($L_TP$) 222 (e.g., where some unbound ligands 220 also can remain). The feed fluid 160 is removed from the membrane 108 as a permeate fluid 162 in which at least some of the protein analyte P has been removed from the feed 160 (e.g., complete or substantially complete removal of the protein analyte P provided that the membrane 108 binding capacity is not exceeded). Optionally, the protein analyte P can be recovered/removed from the membrane 108 (e.g., to recover the protein analyte P as a product and/or to regenerate the membrane 108 for further use). An elution/wash fluid 164 is fed to the membrane, removing at least some (or all) of the protein analyte P from the analyte-bound ligand groups ($L_TP$) 222 to provide an eluate/purified permeate fluid 166 including the protein analyte P.

EXAMPLES

The following examples illustrate the disclosed processes and compositions, but are not intended to limit the scope of any claims thereto.

Figure 2A:
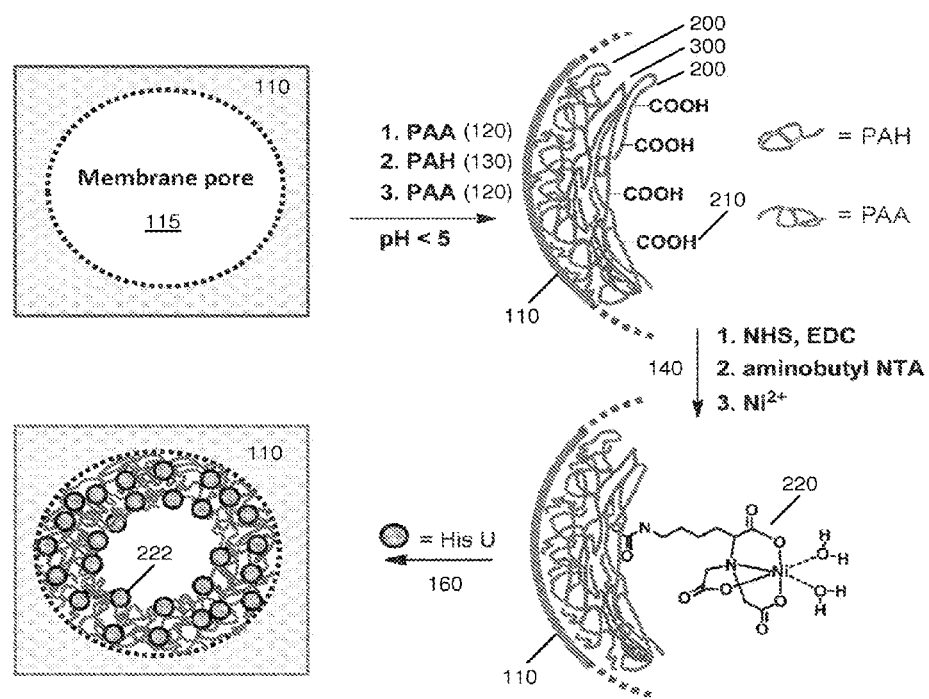
FIG. 2A is a schematic showing polyelectrolyte immobilization within membrane pores, derivatization of the surface layer of PAA with NTA-$Ni^{2+}$ complexes, and protein binding to the modified membrane. Abbreviations: PAA-poly(acrylic acid), PAH-protonated poly(allylamine), NHS-N-hydroxysuccinimide, EDC-N-(3-dimethylaminopropyl)-N'-ethylcarbodiimide hydrochloride, NTA-nitrilotriacetate, HisU-His-tagged ubiquitin.
Figure 2B:
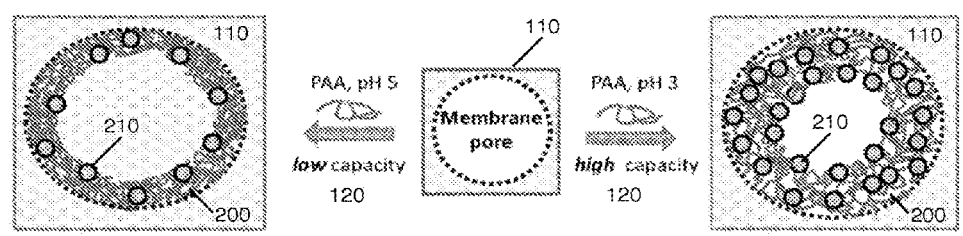
FIG. 2B is a comparative illustration of relative functional group density and capture capacity for adsorbed PAA at pH=5 (left) and pH=3 (right).

FIGS. 2A and 2B illustrate specific examples of the general embodiments illustrated in FIGS. 1A to 1E and as described in Examples 1-5 below. FIG. 2A illustrates a membrane 100 first functionalized with sequential polyacrylic acid 200, poly(allyl amine hydrochloride) 300, and polyacrylic acid 200 layers. The acid-functionalized membrane 104 is then further derivatized with aminobutyl nitrilotriacetic acid and nickel to provide a protein-binding functionalized membrane 108 including a nickel-ligand complex 220 amide-linked to the polyacrylic acid 200 layer and capable of binding polyhistidine-tagged proteins (e.g., polyhistidine-tagged ubiquitin 160 captured to form bound ubiquitin 222 in the membrane). FIG. 2B qualitatively illustrates an advantage of forming the adsorbed polyacid layer(s) 200 at low pH values according to the disclosure, namely including the relatively higher density of free acid groups 210 (e.g., usable as is or derivatizable to other ligands 220 for specific binding to various analytes).

Examples 1-5: Porous Membrane Functionalization with Adsorbed Poly(Acrylic Acid)

Layer-by-layer polyelectrolyte adsorption is a simple, convenient method for introducing ion-exchange sites in porous membranes. This example demonstrates that adsorption of poly(acrylic acid) (PAA)-containing films at pH 3 rather than pH 5 increases the protein-binding capacity of such polyelectrolyte-modified membranes 3- to 6-fold. The low adsorption pH generates a high density of —COOH groups that function as either ion-exchange sites or points for covalent immobilization of metal-ion complexes that selectively bind tagged proteins. When functionalized with nitrilotriacetate (NTA)-$Ni^{2+}$ complexes, membranes containing PAA/polyethyleneimine (PEI)/PAA films bind 93 mg of histidine$_6$-tagged (His-tagged) Ubiquitin per $cm^3$ of membrane. Additionally these membranes isolate His-tagged COP9 signalosome complex subunit 8 from cell extracts and show >90% recovery of His-tagged proteins. Although modification with polyelectrolyte films occurs by simply passing polyelectrolyte solutions through the membrane for as little as 5 min, with low-pH deposition the protein binding capacities of such membranes are as high as for membranes modified with polymer brushes and 2-3 fold higher than for commercially available IMAC resins. Moreover, the buffer permeabilities of polyelectrolyte membranes that bind His-tagged protein are ~30% of the corresponding permeabilities of unmodified membranes, so protein capture can occur rapidly with low pressure drops. Even at a solution linear velocity of 570 cm/h, membranes modified with PAA/PEI/PAA exhibit a lysozyme dynamic binding capacity (capacity at 10% breakthrough) of ~40 mg/$cm^3$. Preliminary studies suggest that these membranes are stable under depyrogenation conditions (1 M NaOH).

Porous membranes modified with affinity ligands offer a potential solution to some of the challenges in column-based affinity separations. Convection through the membrane pores and short radial diffusion distances provide rapid protein transport to binding sites, and increasing the membrane surface area is a relatively straightforward strategy to scale up membrane processes. Unfortunately, membrane adsorbers suffer from low binding capacities relative to traditional columns. A number of research groups successfully modified membranes with polymer brushes to increase the number of binding sites and enhance binding capacity, but brush growth is a relatively cumbersome process, frequently requiring both deposition of initiator molecules and polymerization under anaerobic conditions.

The layer-by-layer (LbL) adsorption at pH values of 4 or higher of polyelectrolyte multilayers in nylon with 5 μm pores was previously examined and it was determined that it could effectively create ion-exchange membranes. Modification of membranes using LbL adsorption, which simply involves passing a few aqueous solutions through the membrane, is extremely convenient, but the lysozyme binding capacities of those membranes were at most 16 mg/$cm^3$. Commercial ion-exchange Mustang S membranes already show lysozyme binding capacities of 45-50 mg/$cm^3$.

These examples demonstrate that control of the pH employed during deposition of weak polyelectrolytes can greatly increase the protein-binding capacities of membranes modified with polyelectrolyte multilayers. A number of papers report that changes in the deposition pH of poly(acrylic acid) (PAA)/protonated poly(allyl amine)

(PAH) multilayer coatings greatly alter film properties including thickness, swelling, metal adsorption capacity, permeability, and biocompatibility. Additionally, recent work shows that deposition of (PAH/PAA)$_n$ films on flat surfaces at pH 3 rather than pH 5 leads to a ~6-fold increase in lysozyme adsorption. Thus it is thought that in membranes, PAH/PAA adsorption at low pH would give a high density of free —COOH groups that bind cationic proteins through ion-exchange interactions. (By free, the meaning is that the —COOH groups are not deprotonated and not ion-paired with neighboring ammonium groups of PAH during deposition.) Moreover, derivatization of the free —COOH groups by reaction with aminobutyl nitrilotriacetate (NTA) should yield metal-ion complexes that selectively bind tagged proteins (FIGS. 2A-2B). Remarkably, membranes modified with PAA/polycation/PAA films deposited at pH 3 bind as much as 120 mg lysozyme per cm$^3$ of membrane, which is comparable to the capacities of the best membranes modified with polymer brushes. Additionally, after derivatization with NTA-Ni$^{2+}$ complexes, these membranes can capture His-tagged proteins from cell extracts and facilitate 95% protein recovery at high purity. The simplicity of LbL adsorption and the high performance of these membranes make them very attractive for protein purification.

Materials: Hydroxylated nylon (LOPRODYNE LP, Pall, 1.2 μm pore size, 110 μm thick), nylon (GE, non-hydroxylated, 1.2 μm pore size, average thickness 95 μm), and polyethersulfone (GE, 1.2 μm pore size, average thickness 130 μm) membranes were cut into 25 mm-diameter discs prior to use. Unless specified, all proteins and chemicals were obtained from Sigma-Aldrich. Coomassie protein assay reagent (Thermo Scientific), Histidine$_6$-tagged Ubiquitin (HisU, human recombinant, Enzo Life Sciences), concanavalin A (Con A) from *Canavaliaensiformis* (Jack bean), albumin from chicken egg white; lysozyme from chicken egg white; bovine serum albumin (BSA), and β-Lactoglobulin B from Bovine milk were used as received. His-tagged COP9 signalosome complex subunit 8 (CSN 8) was overexpressed in BL21DE3 cells as described below. Buffers were prepared using analytical grade chemicals and deionized water (Milli-Q, 18.2 MΩ cm). Poly(sodium 4-styrenesulfonate) (M$_w$=70,000), poly(allylamine hydrochloride) (M$_w$=120,000-210,000, Alfa-Aesar), polyethyleneimine (branched, M$_w$=25,000), poly(acrylic acid) (M$_w$=90,000, 25% aqueous solution, Polysciences), TWEEN-20 surfactant, N-(3-dimethylaminopropyl)-N-ethylcarbodiimide hydrochloride (EDC), N-hydroxysuccinimide, and Na,Na-bis(carboxymethyl)-L-lysine hydrate (aminobutyl NTA) were used without further purification.

Example 1: PAA Adsorption and Metal-Binding Capacity

Membrane modification: Membrane discs were cleaned for 10 min with UV/ozone and placed in a homemade TEFLON™ holder (similar to an Amicon cell) that exposed 3.1 cm.sup.2 of external membrane surface area. Subsequently, a 20 mL solution containing 0.02 M PSS and 0.5 M NaCl was circulated through the membrane for 40 min at a flow rate of 1 mL/min using a peristaltic pump. Additional polycation (PAH or PEI) and polyanion (PAA) layers were deposited similarly using 0.5 M NaCl solutions containing 0.01 M PAA or 0.02 M PAH or 2 mg/mL PEI. After deposition of each polyelectrolyte, 20 mL of water was passed through the membrane at the same flow rate. The pH of the PSS solution was 4.7, and PAA, PAH, and PEI deposition solutions were adjusted to different values with 1 M NaOH or 1M HCl. Membrane hydraulic permeabilities were determined as described previously.

To derivatize PAA side chains in adsorbed films, 10 mL of 0.1 M NHS, 0.1 M EDC in water were circulated through the membrane for 1 h prior to rinsing with 20 mL of deionized water and 10 mL of ethanol. Subsequently, 10 mL of aqueous aminobutyl NTA (0.1 M, pH 10.2) was circulated through the NHS-modified substrate for 1 h followed by rinsing with 20 mL of water. Finally, the NTA-Cu$^{2+}$ (or Ni$^{2+}$) complex was formed by circulating 10 mL of aqueous 0.1 M CuSO$_4$ (or NiSO$_4$) through the membrane for 2 h followed by rinsing with water. The substrate was dried with N$_2$ prior to protein binding.

Adsorption of Polyelectrolytes in Hydroxylated Nylon Membranes:

Previous work has shown that PSS serves as a robust adhesion layer for deposition of polyelectrolyte multilayers in a variety of membranes. Multiple hydrophobic interactions likely lead to strong PSS adsorption. A PAH/PAA bilayer was deposited on PSS adsorbed in a 1.2 μm nylon membrane. This procedure requires no organic solvents or anaerobic conditions and is much simpler than modification of membranes with polymer brushes. Moreover, because the fraction of ionized —COOH groups on an adsorbed PAA monolayer varies from <10% to >60% on going from pH 2 to pH 5, variation of deposition pH provides an important variable for modifying film properties. Deposition of PAA at low pH leads to films that contain free —COOH groups, and subsequent derivatization or deprotonation of these groups should lead to a high density of protein-binding sites.

Figure 3A:
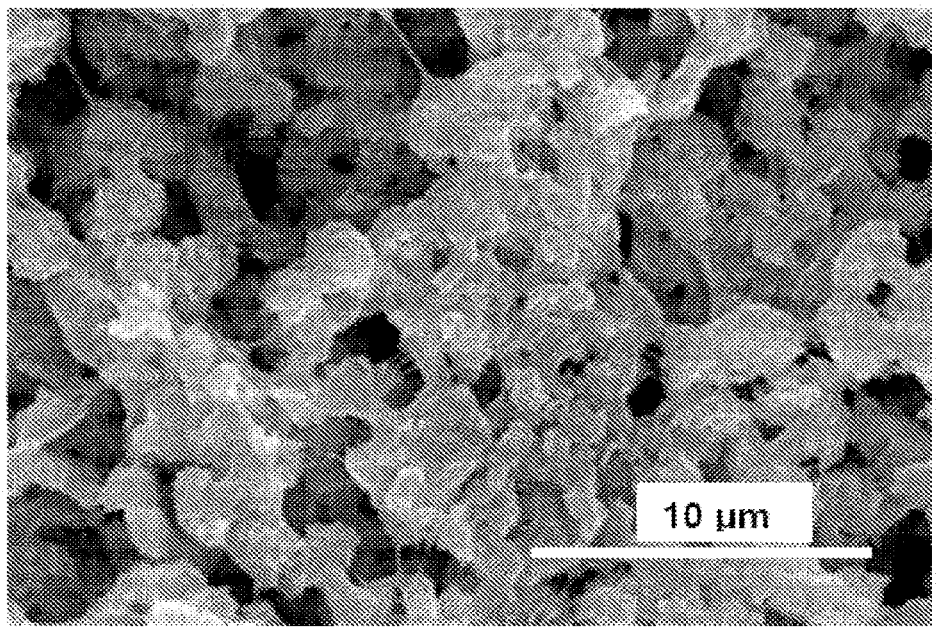
FIGS. 3A-3C are scanning electron micrograph (SEM) images of a bare nylon membrane with nominal 1.2 μm pores (FIG. 3A), and similar membranes modified with PSS/PAH/PAA deposited at pH 2 (FIG. 3B) and pH 5 (FIG. 3C).
Figure 3B:
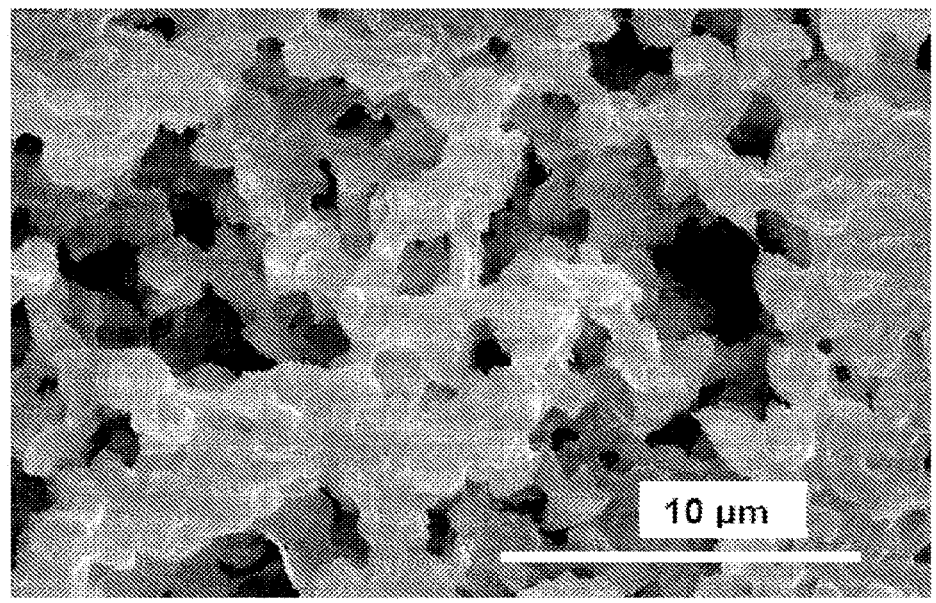
Figure 3C:
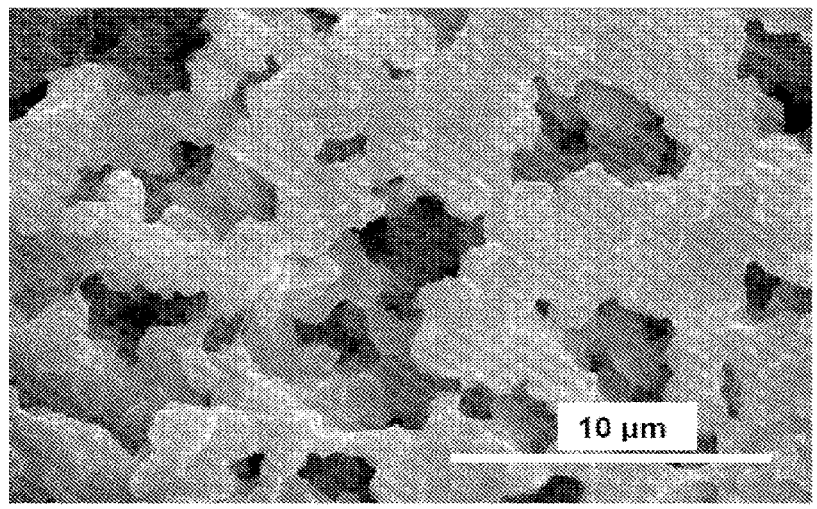

Monitoring polyelectrolyte adsorption in nylon membranes is challenging. SEM images suggest a decrease in porosity after deposition of polyelectrolytes, but such images are only qualitative and do not reflect film swelling (FIGS. 3A-3C). The water permeability of nylon membranes decreases significantly after polyelectrolyte adsorption, and the decrease is most significant for deposition of polyelectrolytes at low pH (Table 1 below). Moreover, with film deposition at low pH, membrane permeability increases after derivatization with NTA-Cu$^{2+}$ complexes, presumably because of a decrease in swelling (Table 2 below). Nevertheless, in control experiments, even bare nylon membranes showed a 30-50% decline in hydraulic pure water permeability after exposure to 20 mM phosphate buffer (pH 7.4). Thus, although water permeabilities suggest greater polyelectrolyte adsorption at low pH, they do not provide a quantitative measure of polyelectrolyte adsorption.

TABLE 1

Water permeabilites of nylon membranes before and after modification with different films.$^a$

| Polyelectrolyte films in nylon membrane | pH of PAH and/ or PAA deposition solutions | Water permeability of unmodified membrane (mL/cm$^2$ min atm) | Water permeability of modified membrane (mL/cm$^2$ min atm) | Reduction of water permeability (%) |
|---|---|---|---|---|
| PSS/PAH/ PAA | 2 | 114 ± 10 | 57 ± 4 | 50 ± 10 |
| | 3 | 107 ± 17 | 34 ± 11 | 68 ± 22 |
| | 4 | 116 ± 6 | 75 ± 11 | 35 ± 11 |
| | 5 | 120 ± 18 | 79 ± 32 | 34 ± 31 |
| PAA | 2 | 116 ± 10 | 42 ± 8 | 64 ± 12 |
| | 3 | 143 ± 11 | 46 ± 15 | 68 ± 14 |
| | 4 | 122 ± 5 | 111 ± 4 | 9 ± 5 |
| | 5 | 136 ± 23 | 128 ± 22 | 6 ± 23 |

TABLE 1-continued

Water permeabilites of nylon membranes before and after modification with different films.[a]

| Poly-electrolyte films in nylon membrane | pH of PAH and/or PAA deposition solutions | Water permeability of unmodified membrane (mL/cm² min atm) | Water permeability of modified membrane (mL/cm² min atm) | Reduction of water permeability (%) |
|---|---|---|---|---|
| PAA/PAH/PAA | 3 | 114 ± 7 | 25 ± 5 | 78 ± 9 |
| PAA/PEI/PAA | 3 | 123 ± 7 | 69 ± 3 | 44 ± 7 |

[a]Each experiment was performed with two different membranes, and the ±values represent the difference between the average and the data points.

TABLE 2

Water permeabilites of nylon membranes before and after modification with different films derivatized with NTA—$Cu^{2+}$.[a]

| Poly-electrolyte films in nylon membrane | pH of PAH and/or PAA deposition solutions | Water permeability of unmodified membrane (mL/cm² min atm) | Water permeability of modified membrane (mL/cm² min atm) | Reduction of water permeability (%) |
|---|---|---|---|---|
| PSS/PAH/PAA | 2 | 105 ± 3 | 77 ± 6 | 27 ± 6 |
|  | 3 | 123 ± 3 | 98 ± 5 | 20 ± 5 |
|  | 4 | 123 ± 2 | 56 ± 1 | 55 ± 2 |
|  | 5 | 131 ± 5 | 39 ± 5 | 70 ± 6 |
| PAA | 2 | 86 ± 1 | 75 ± 2 | 13 ± 3 |
|  | 3 | 89 ± 1 | 68 ± 2 | 24 ± 3 |
|  | 4 | 90 ± 2 | 80 ± 2 | 11 ± 3 |
|  | 5 | 80 ± 2 | 74 ± 1 | 7.5 ± 3 |
| PAA/PAH/PAA | 3 | 118 ± 4 | 59 ± 2 | 50 ± 4 |
| PAA/PEI/PAA | 3 | 123 ± 1 | 77 ± 2 | 38 ± 2 |

[a]Each experiment was performed with two different membranes, and the ±values represent the difference between the average and the data points.

The amount of $Cu^{2+}$ that binds to membranes modified with PSS/PAH/PAA-NTA-$Cu^{2+}$ likely reflects the density of free —COOH groups in the membrane. Table 3 (column 5) shows that the quantity of $Cu^{2+}$ captured in these membranes dramatically increases with a decrease in the pH of PAH and PAA adsorption. This increase likely reflects enhancements in both the film thickness and availability of free —COOH or —COO⁻ groups for activation and reaction with aminobutyl NTA. Considering the membrane modified with PSS/PAH/PAA-NTA using a deposition pH of 2, the $Cu^{2+}$ binding capacity of 15 mg/cm³ suggests that there is ~75 mg/cm³ of polymer in the membrane. This estimation assumes complete derivatization to give a repeat unit molecular weight of 316 for PAA-NTA and neglects the amount of PSS and PAH in the membranes as well as PAA repeat units that interact with PAH and cannot be derivatized. The total amount of polymer in the membrane could easily be twice the calculated value.

While a PSS adhesion layer is important for forming stable polyelectrolyte films in nylon membranes, adsorption of PAA directly in nylon pores without an adhesion layer also provides a remarkably simple way to introduce a high density of functional groups in these systems. In principle PAA might adsorb to nylon membranes through hydrophobic interactions or hydrogen bonds. Similar to membranes modified with PSS/PAH/PAA, the $Cu^{2+}$-binding capacities of PAA films deposited at pH 2 and pH 3 and subsequently modified with aminobutyl NTA are 4- to 6-fold higher than the capacities of corresponding films deposited at pH 4 and 5 (Table 3, column 5). Thus the total amount of adsorbed PAA may be ~5-fold higher when comparing films deposited at pH 2 or 3 with films deposited at pH 5. Notably, for films deposited at low pH, the $Cu^{2+}$ binding is similar for membranes modified with PAA and PSS/PAH/PAA films.

TABLE 3

Lysozyme and $Cu^{2+}$ binding capacities of nylon membranes modified with different films.[a]

| Polyelectrolyte films in nylon membrane | pH of PAH and/or PAA deposition solutions | Lysozyme binding from breakthrough curves (mg/cm³) | Lysozyme binding From elution (mg/cm³) | $Cu^{2+}$ binding (mg/cm³)[c] |
|---|---|---|---|---|
| PSS/PAH/PAA | 2 | 90 ± 1 | 87 ± 1 | 15 ± 1 |
|  | 3 | 106 ± 2 | 106 ± 6 | 11 ± 2 |
|  | 4 | 49 ± 2 | 49 ± 1 | 6 ± 1 |
|  | 5 | 37 ± 4 | 33 ± 3 | 3 ± 2 |
| PAA | 2 | 78 ± 1 | 77 ± 1 | 12 ± 2 |
|  | 3 | 89 ± 4 | 89 ± 2 | 13 ± 2 |
|  | 4 | 22 ± 9 | 22 ± 6 | 4 ± 2 |
|  | 5 | 14 ± 6 | 14 ± 2 | 2 ± 1 |
| PAA/PAH/PAA | 3 | 107 ± 2 | 115 ± 2 | 14 ± 1 |
| PAA/PEI/PAA | 3 | 120 ± 6 | 130 ± 4 | 18 ± 2 |
| PAA/PEI/PAA[b] | 3 | 101 ± 5 | 112 ± 4 | — |

[a]Each experiment was performed with two different membranes, and the ±values represent the difference between the average and the data points.
[b]Lysozyme flow rate of 30 mL/min. In all other cases the lysozyme flow rate was 1 mL/min.
[c]Binding capacity after derivatization with aminobutyl NTA.

Adsorption of a PAH/PAA or PEI/PAA bilayer on a PAA base layer can in principle increase the number of free —COOH groups in a membrane. However, membranes modified with PAA-NTA, PAA/PAH/PAA-NTA, and PAA/PEI/PAA-NTA bind only 12±2, 13±1, and 18±2 mg $Cu^{2+}$/cm³, respectively (all films were deposited at pH 3, as film stability at pH 2 was a concern). Only the PAA/PEI/PAA-NTA coating shows significantly more $Cu^{2+}$ sorption than simple PAA-NTA films. The relatively small increase in bound $Cu^{2+}$ with the addition of the polycation/PAA bilayer reflects the formation of ion pairs between the polycations and underlying PAA and perhaps less extension of the outer PAA layer when adsorption occurs on the polycation rather than directly on a membrane. Notably, adsorption of PAA on the branched PEI apparently leads to more derivatizable —COOH groups than adsorption on linear PAH.

In addition to NTA, $Cu^{2+}$ may bind to underivatized —COOH groups and complicate the interpretation of $Cu^{2+}$ binding data. Thus, $Cu^{2+}$ binding was compared to PAA/PEI/PAA and PAA/PEI/PAA-NTA membranes. The binding was ~30% higher for the NTA-derivatized membrane, but significant binding does occur to the PAA/PEI/PAA film. This is not surprising given the large number of free —COOH groups in the film. Even with the NTA-derivatized coating some fraction of the $Cu^{2+}$ binding likely occurs to underivatized —COOH groups. Attempts to selectively elute the $Cu^{2+}$ binding to underivatized —COOH groups were unsuccessful.

Plugging of membrane pores is always a potential problem when modifying membranes by adsorption. The permeability of membranes to pH 7.4 phosphate buffer (20 mM) decreases from around 70 to 20 mL/(cm² min atm) when comparing a bare membrane and a membrane containing a PAA/PEI/PAA film. Although this is a significant decline in permeability, rapid flow through the membrane can still occur using a simple peristaltic pump, even after derivatization with NTA. In contrast, the permeability of PAA/PEI/PAA-modified membranes to deionized water after treatment with buffer is <1 mL/(cm² min atm). Extension of deprotonated PAA at low ionic strength evidently blocks pores, so filtration should occur with at least small amounts of salt. Rinsing membranes with 2.7 mM HCl protonates —COOH groups, and the resulting collapse of polymers restores water permeability to around 100 mL/(cm² min atm). Subsequent exposure to pH 7.4 buffer again decreases permeability. These results are consistent with prior studies of pH-responsive membranes.

Example 2: Lysozyme Binding by Adsorbed PAA

A solution of lysozyme (0.30 or 0.45 mg/mL) in 20 mM phosphate buffer (pH 7.4) was pumped through the modified membrane at a flow rate of 1 or 30 mL/min, and the permeate was collected for analysis at specific time intervals. Subsequently, the membrane was rinsed with 20 mL of washing buffer A (20 mM phosphate buffer with 0.1% Tween 20, pH 7.4) followed by 20 mL of phosphate buffer. The protein was then eluted using 5-10 mL of 20 mM phosphate buffer (pH 7.4) containing 1 M KSCN. Unless specified, flow rates were 1 mL/min.

Figure 4:
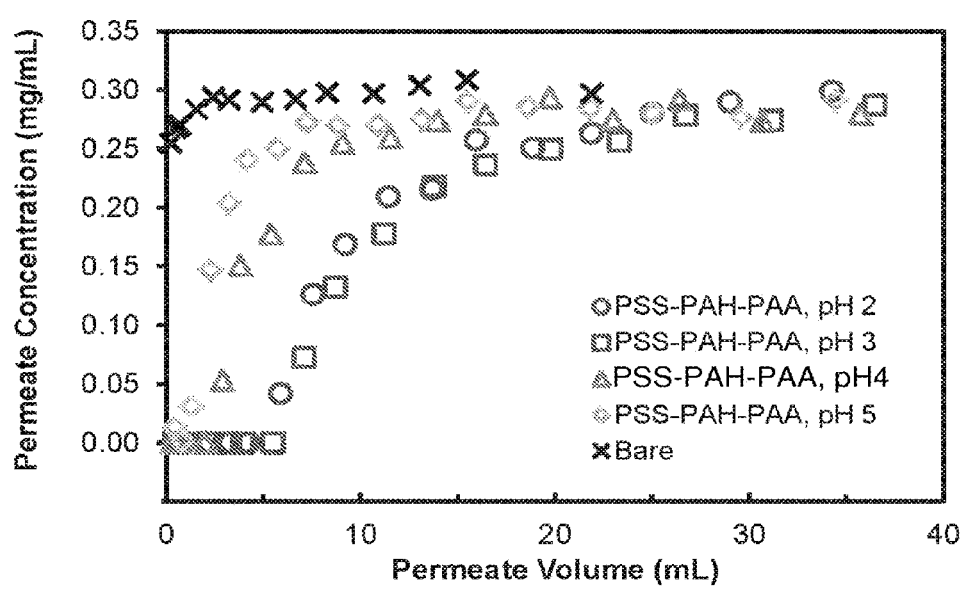
FIG. 4 illustrates breakthrough curves for the passage of 0.3 mg/mL lysozyme through a bare nylon membrane and nylon membranes modified with PSS/PAH/PAA films deposited at different pH values. The protein-solution flow rate was 1 mL/min, which corresponds to a linear velocity of 19 cm/h above the membrane.

Lysozyme Binding to Hydroxylated Nylon Membranes Modified with Polyelectrolyte Films:

Deposition of polyanion-terminated films in membrane pores creates cation-exchange sites that bind positively charged proteins such as lysozyme (molecular weight 14.3 kDa), which at pH 7.4 has a charge of +8. FIG. 4 presents breakthrough curves for passage of 0.3 mg/mL lysozyme (in pH 7.4 buffer) through nylon membranes modified with PSS/PAH/PAA films deposited at several pH values. When protein begins to saturate the binding sites, the lysozyme breaks through the membrane, and its effluent concentration eventually reaches that of the feed solution. The later breakthrough in the case of films deposited at pH 2 and 3 demonstrates the higher binding capacities in these systems. Integration of the differences between the feed concentration and the effluent concentration gives the membrane binding capacity, and Table 3 (column 3) shows that the lysozyme binding capacity for PSS/PAH/PAA films deposited at pH 3 is 3 times that for films adsorbed at pH 5. Thicker films and higher concentrations of free —COOH groups, as indicated by $Cu^{2+}$ binding capacities (Table 3, column 5), presumably lead to more binding sites for membranes modified by polyelectrolyte adsorption at low pH. The highest binding at pH 3 rather than pH 2 might relate to film conformation. Binding capacities determined from elution of the lysozyme with 20 mM phosphate buffer (pH 7.4) containing 1 M KSCN agree well with those determined from the breakthrough curves (compare columns 3 and 4 of Table 3).

Figure 5:
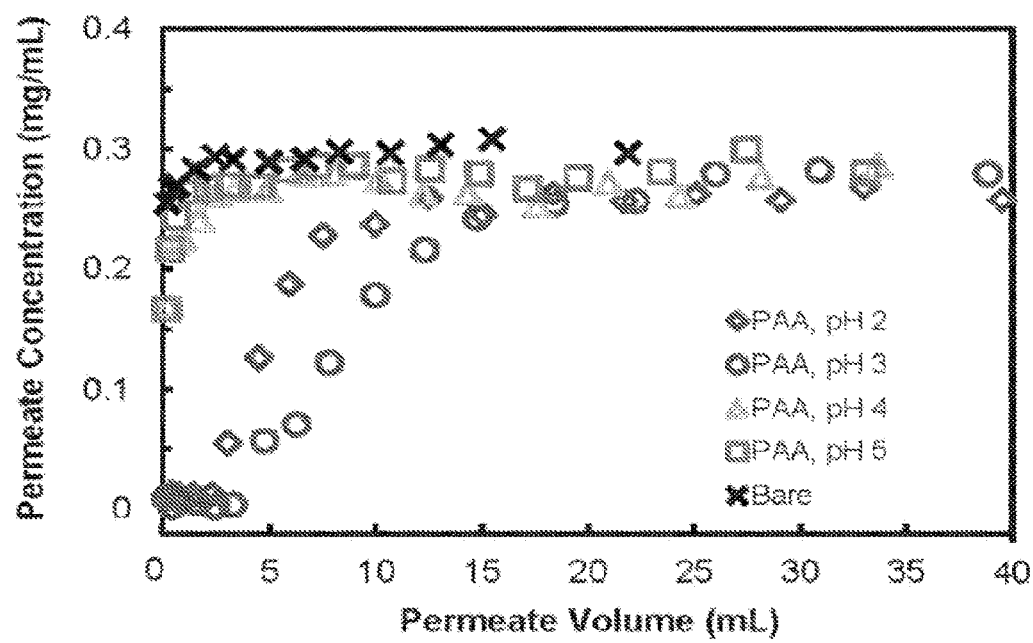
FIG. 5 illustrates breakthrough curves for the passage of 0.3 mg/mL lysozyme through nylon membranes modified with single layers of PAA adsorbed at various pH values. The protein solution flow rate was 1 mL/min, which corresponds to a linear velocity of 19 cm/h above the membrane.
Figure 6:
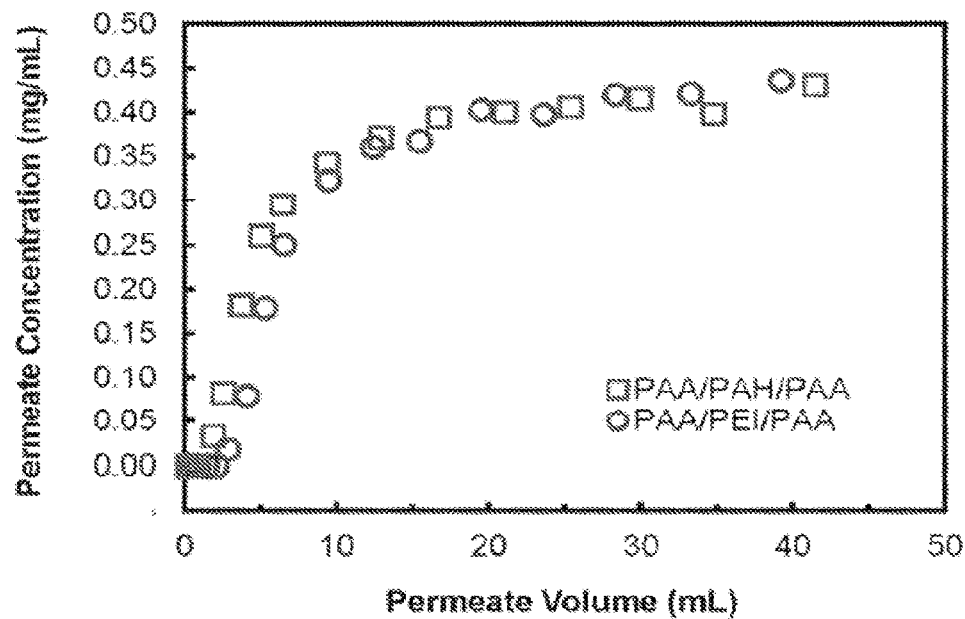
FIG. 6 illustrates breakthrough curves for the passage of 0.45 mg/mL lysozyme through nylon membranes modified with PAA/PAH/PAA or PAA/PEI/PAA multilayers. The pH of the PAA, PAH, and PEI deposition solutions was 3, and the protein solution flow rate was 1 mL/min.

Table 3 also shows the lysozyme binding capacities of membranes modified by adsorption of PAA, PAA/PAH/PAA, and PAA/PEI/PAA films. FIGS. 5 and 6 show representative breakthrough curves. Maximum binding using a single PAA layer occurs for films deposited at pH 3, which is consistent with the high $Cu^{2+}$ binding for this membrane (see Table 3, column 5). PAA/PAH/PAA or PAA/PEI/PAA multilayers provide 20-30% higher binding capacities than single PAA layers, with the PAA/PEI/PAA film showing especially high capacities. This high lysozyme adsorption with PAA/PEI/PAA agrees well with data for $Cu^{2+}$ binding.

To further simplify film formation, adsorption time was reduced from 40 min to 5 min for deposition of each polyelectrolyte. Rinsing time was also decreased from 20 min to 5 min. The binding capacity of PAA/PEI/PAA-containing membranes modified using the short deposition times is 108±1 mg/cm³, so reducing the total deposition time 6-fold decreased the binding capacity only 10%. By reducing the adsorption time, complete deposition of a PAA/PEI/PAA film requires only 30 min. Binding capacities are more than 6-fold greater than those in a prior study in part due to the low pH deposition but also because the membranes have smaller pores (1.2 μm versus 5 μm) that lead to higher surface areas.

Figure 7:
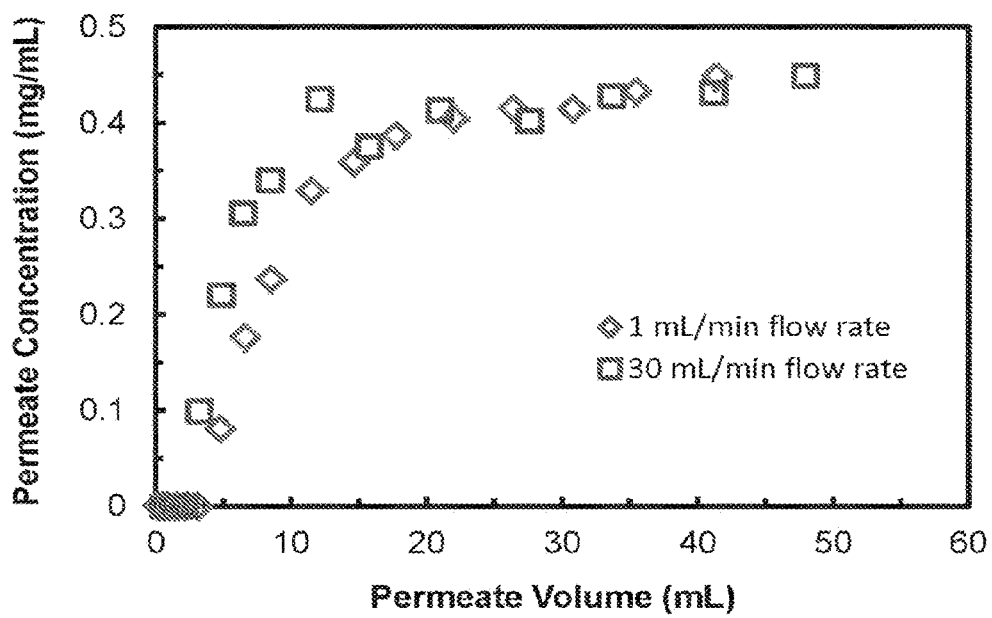
FIG. 7 illustrates breakthrough curves for the passage of 0.45 mg/mL lysozyme through a PAA/PEI/PAA-modified (deposition pH of 3) nylon membrane at flow rates of 1 mL/min (blue diamonds) and 30 mL/min (red squares).

Protein Binding as a Function of Flow Rate:

Compared to column-based methods, membrane adsorbers are particularly attractive for rapid protein capture because radial diffusion distances are short, and convection brings proteins to binding sites. Moreover, rapid flow rates are possible because of modest pressure drops. If dynamic capacity is defined as the amount of protein bound when breakthrough reaches 10%, typical dynamic capacities for the protein binding studies described above are about ⅓ of the equilibrium binding capacities. However, these experiments all employed flow rates of 1 mL/min. To better examine the dynamics of protein binding, breakthrough curves were compared for lysozyme binding to PAA/PEI/PAA-modified membranes at solution flow rates of 1 and 30 mL/min. These flow rates correspond to linear velocities of 19 cm/h and 570 cm/h, and residence times of ~1000 msec and 35 msec, respectively. (Note that these residence times assume a membrane porosity of 50%, whereas the linear velocity is that above the membrane.) As FIG. 7 shows, the breakthrough curves are not very different at the two flow rates and dynamic capacities are similar (within about 25%).

Polyelectrolyte Films in Other Membrane Materials:

As a test of the versatility of layer-by-layer adsorption for membrane modification, polyelectrolyte layers were immobilized in PES and non-hydroxylated nylon membranes and lysozyme binding was studied with these systems. For non-hydroxylated membranes, PSS/PAH/PAA and PAA/PEI/PAA films were deposited using a deposition pH of 3 for all polyelectrolytes except PSS. The lysozyme binding capacities for the PSS/PAH/PAA- and PAA/PEI/PAA-modified membranes were 68±3 mg/cm³ and 72±5 mg/cm³, respectively, or about 60% of the binding capacities for corresponding hydroxylated nylon membranes. The drop in binding capacity could stem either from less adsorption to the non-hydroxylated membrane or a difference in the surface areas of the two substrates. After treating the non-hydroxylated membranes with phosphoric acid in formalin to introduce hydroxyl groups, PAA/PEI/PAA adsorption leads to a lysozyme binding capacity of 103±2 (105±7 from elution) mg/cm³. Assuming that the formaldehyde treatment does not increase surface area, this result suggests that hydroxylation increases the quantity of polyelectrolyte adsorption. Unfortunately, PES membranes plugged during deposition of PSS/PAH/PAA and PAA/PEI/PAA films. The membrane geometry is obviously a crucial factor in determining whether polyelectrolyte adsorption can occur without plugging the membrane. When a monolayer of PAA (deposition pH of 3) was immobilized in the PES membrane, the lysozyme binding capacity was only 21±7 mg/cm³, or about 25% of that for a similar hydroxylated nylon membrane. Selection of the appropriate membrane substrate is thus vital to optimizing membranes modified with polyelectrolytes.

Stability of Membranes Modified with PAA/PEI/PAA:

In studies of the stability of membranes modified with PAA/PEI/PAA, two membranes were employed for 6 repetitions of lysozyme binding and elution. The binding capacity ranged from 125 to 141 mg/cm³ over the 6 replicates. Thus the membranes are stable, although declining flow rates were observed during the 6$^{th}$ experiment for both modified membranes. Note that this stability occurs even when using 1 M KSCN for protein elution.

Stability of modified membranes was also tested under depyrogenation conditions. In this case, lysozyme was first bound in nylon membranes modified with PAA/PEI/PAA films deposited at pH 3. After lysozyme elution with 1 M KSCN, 10 mL 1 N NaOH was circulated through the modified membranes for 1 h and the binding experiment was repeated. The binding capacities before and after treatment with 1 M NaOH were 131±1 mg/cm$^3$ and 129±3 mg/cm$^3$ respectively. Thus, treatment of the membranes with NaOH to remove or disable toxins prior to reuse might be feasible.

Example 3: Con A and HisU Binding by Derivatized Adsorbed PAA

Con A and HisU solutions (0.3 mg/mL) were prepared in 20 mM phosphate buffer at pH 6 and 7.4, respectively. For Con A, washing buffer B (20 mM phosphate buffer containing 0.1% Tween-20 surfactant and 0.15 M NaCl) and elution buffer (20 mM phosphate buffer containing 50 mM EDTA) were also adjusted to pH 6. In the case of HisU, the washing buffer B and elution buffer (0.5 M NaCl, 0.5 M imidazole in 20 mM phosphate buffer) were maintained at pH 7.4. For both Con A and HisU, membranes were loaded with buffered protein solution, rinsed with 20 mL washing buffer B followed by 20 mL phosphate buffer at pH 6 or 7.4, and eluted with 8-9 mL of elution buffer. The concentrations of protein in loading, rinsing, and eluate solutions were determined using a Bradford assay. Each Con A binding capacity was determined with two membranes, and the ± values represent the difference between the average and the data points.

Figure 8:
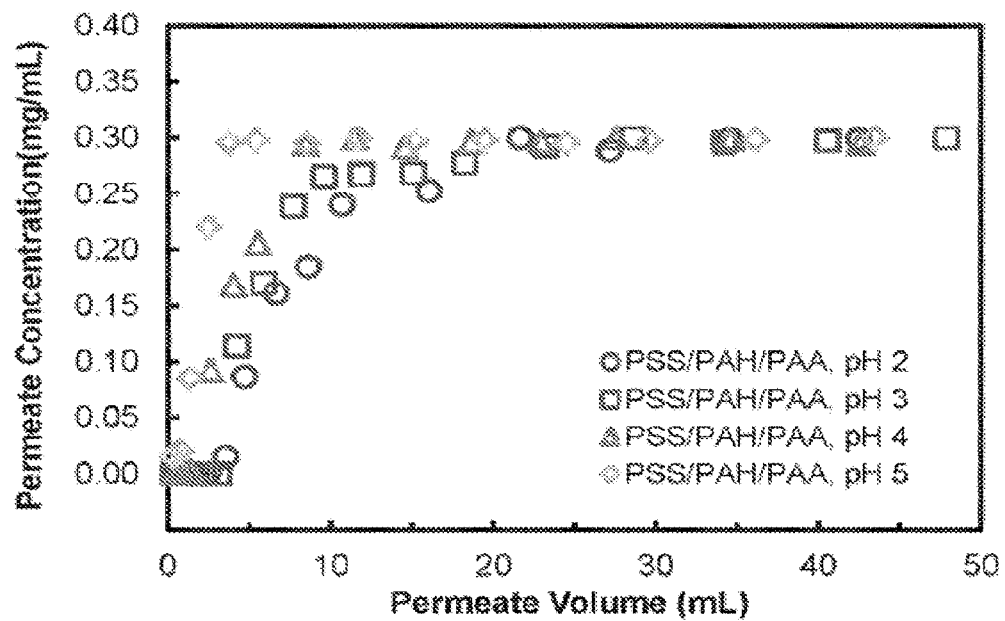
FIG. 8 illustrates breakthrough curves for the passage of 0.3 mg/mL Con A (pH 6, 20 mM phosphate buffer) through nylon membranes modified with PSS/PAH/PAA-NTA-$Cu^{2+}$ films adsorbed at different pH values. The protein solution flow rate was 1 mL/min.
Figure 9:
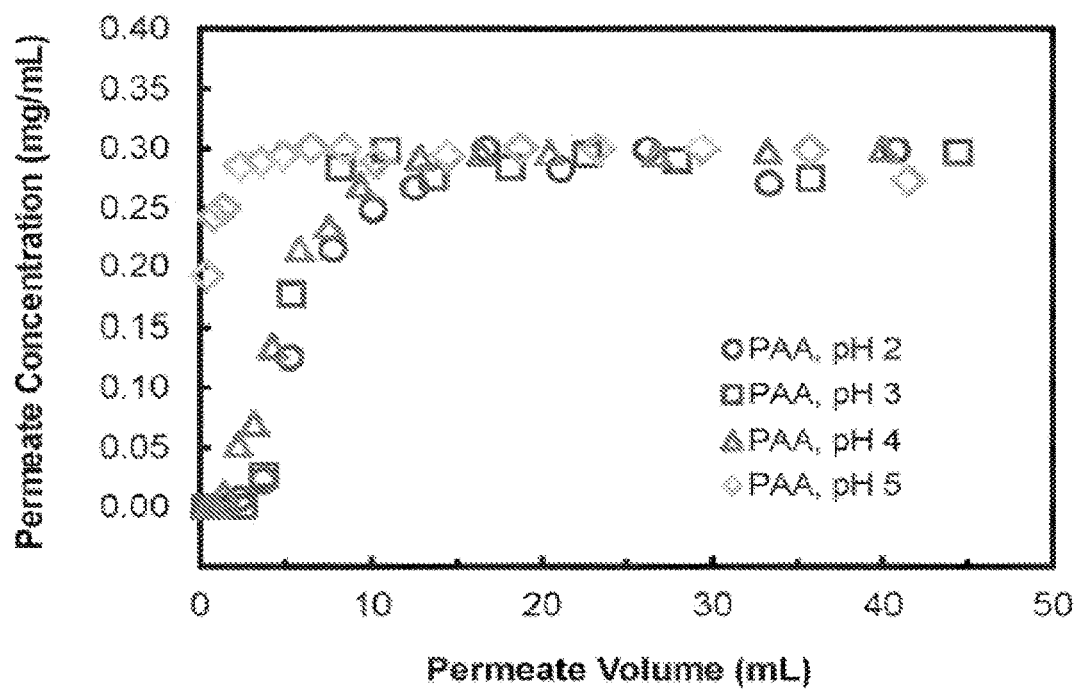
FIG. 9 illustrates breakthrough curves for the passage of 0.3 mg/mL Con A through nylon membranes modified with PAA-NTA-$Cu^{2+}$ films (pH of PAA deposition solutions were varied). The protein solution flow rate was 1 mL/min.
Figure 10:
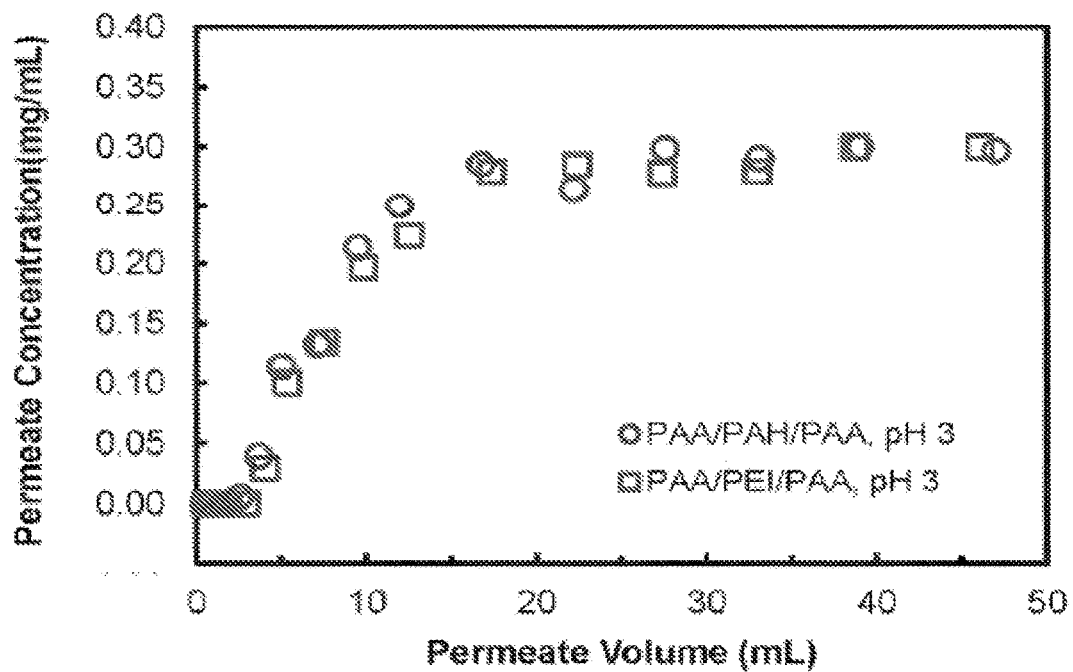
FIG. 10 illustrates breakthrough curves for for the passage of 0.3 mg/mL Con A through nylon membranes modified with PAA/PAH/PAA-NTA-$Cu^{2+}$ and PAA/PEI/PAA-NTA-$Cu^{2+}$ films. The protein solution flow rate was 1 mL/min.

Con A Binding to Membranes with Films Containing NTA-Cu$^{2+}$:

To increase the specificity of protein binding, PAA films were derivatized with metal-ion complexes that bind proteins containing accessible histidine groups. Initially, capture of a readily available protein, Con A, through interaction with NTA-Cu$^{2+}$ complexes was examined. FIGS. 8-10 show representative breakthrough curves for passage of Con A solutions through different modified nylon membranes, and Table 4 presents the protein-binding capacities determined both from breakthrough curves and protein elution. For modification with either PSS/PAH/PAA-NTA-Cu$^{2+}$ or PAA-NTA-Cu$^{2+}$, the Con A binding capacities decrease with an increase in deposition pH, following the trend in the amount of Cu$^{2+}$ bound in the different membranes (Table 3, column 5). Membranes modified with PAA/PEI/PAA-NTA-Cu$^{2+}$ and PAA/PAH/PAA-NTA-Cu$^{2+}$ show the highest Con A-binding capacities (Table 4) of the membranes tested. Deposition of more polyelectrolyte bilayers might increase capacity, but it would also lead to plugging of membrane pores or large decreases in permeability. Overall, Con A binding capacities are ~35% lower than for lysozyme, presumably because the large size of Con A (108 kDa) prevents access to some binding sites. Con A also interacts with different species (metal-ion complexes) in the film.

TABLE 4

Con A binding capacities of hydroxylated nylon membranes modified by different polyelectrolyte films.[a]

| Polyelectrolyte films | pH of PAH and/or PAA deposition solution | Con A binding from breakthrough curve (mg/cm$^3$) | Con A binding from elution (mg/cm$^3$) |
|---|---|---|---|
| PSS/PAH/PAA—NTA—Cu$^{2+}$ | 2 | 65 ± 1 | 69 ± 2 |
|  | 3 | 53 ± 1 | 52 ± 2 |
|  | 4 | 36 ± 4 | 33 ± 2 |
|  | 5 | 19 ± 4 | 21 ± 4 |
| PAA—NTA—Cu$^{2+}$ | 2 | 60 ± 1 | 59 ± 2 |
|  | 3 | 52 ± 2 | 52 ± 6 |
|  | 4 | 37 ± 4 | 37 ± 5 |
|  | 5 | 12 ± 2 | 11 ± 3 |
| PAA/PAH/PAA—NTA—Cu$^{2+}$ | 3 | 69 ± 1 | 71 ± 2 |
| PAA/PEI/PAA—NTA—Cu$^{2+}$ | 3 | 73 ± 4 | 71 ± 7 |

Figure 11:
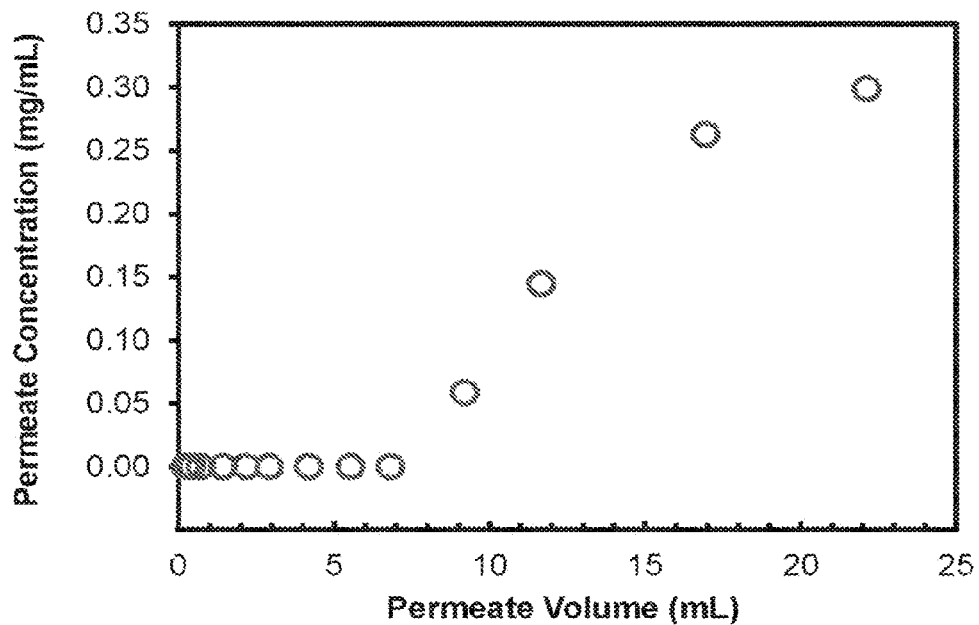
FIG. 11 illustrates breakthrough curve for passage of a 0.3 mg/mL HisU solution through a hydroxylated nylon membrane modified with PAA/PEI/PAA-NTA-$Ni^{2+}$. The feed solution contained 0.3 mg protein/mL, and the solution flow rate was 1.0 mL/min.

[a]Each experiment was repeated with two different membranes, and the ±values represent the difference between the average and the data points HisU Binding to PAA/PEI/PAA-NTA-Ni$^{2+}$-modified Membranes:

Interactions with histidine residues are weaker for NTA-Ni$^{2+}$ than NTA-Cu$^{2+}$, so the incorporation of NTA-Ni$^{2+}$ complexes in columns and membranes allows highly selective binding of proteins that contain polyhistidine tags. In fact, polyhistidine is the most common tag for recombinant protein purification. HisU was employed as a model His-tagged protein to determine the binding capacity of modified nylon membranes. Though HisU is the least expensive His-tagged protein, the high cost of this protein prohibits determining binding capacities on multiple membranes. A PAA/PEI/PAA-NTA-Ni$^{2+}$-modified membrane was selected to determine HisU binding capacity because the related membranes modified with PAA/PEI/PAA-NTA-Cu$^{2+}$ exhibit the most extensive binding of Con A. The breakthrough curve for HisU binding to a PAA/PEI/PAA-NTA-Ni$^{2+}$-modified nylon membrane (FIG. 11) reveals a HisU binding capacity of 93 mg/cm$^3$. The corresponding capacity determined from HisU elution, 97 mg/cm$^3$, is about twice the value of typical binding capacities of commercial IMAC resins and similar to the capacities (88±4 mg/cm$^3$) that were obtained by modifying nylon membranes with polymer brushes. Additionally, the brush-containing membranes are more difficult to prepared and less permeable.

Example 4: Purification of His-U from a Model Protein Mixture

To test protein binding specificity and recovery, a solution containing 0.05 mg/mL (each) His-U, Con A, BSA, Ovalbumin, and β-Lactoglobulin B in 20 mM phosphate buffer (pH 7.4) was prepared. Ten mL of this protein solution was passed through a PAA/PEI/PAA-NTA-Ni$^{2+}$-modified membrane at 1.5 mL/min after the membrane was equilibrated with 20 mL phosphate buffer. Subsequently, the membrane was washed with 20 mL washing buffer C (20 mM phosphate buffer containing 0.1% Tween-20 surfactant and 150 mM NaCl, pH 8.0) and 20 mL phosphate buffer. The bound protein was eluted with 10 mL (2 mL for each fraction) elution buffer (20 mM phosphate buffer with 500 mM imidazole and 500 mM NaCl, pH 8.0). The purity of eluted protein was examined by SDS-PAGE (4-20% gradient gel from Bio-Rad with standard Coomassie blue staining protocols).

Figure 12:
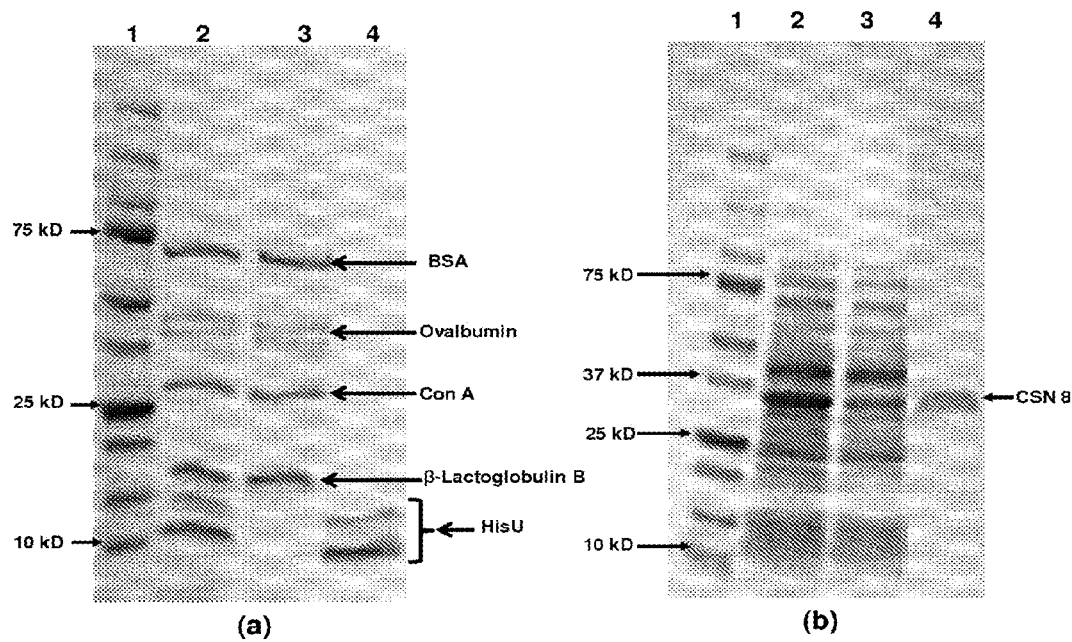
FIG. 12 provides SDS-PAGE analysis (Coomassie blue staining) results of (a) purification of a mixture of BSA, Ovalbumin, Con A, β-Lactoglobulin B, and HisU: lane 1—a protein ladder; lane2—the protein solution; lane 3—the protein solution that passed through the membrane; and lane 4—the eluate from the membrane. (b) purification of CSN 8 from a cell extract: lane 1—a protein ladder; lane 2—a cell extract form BL21DE3 cells with overexpressed His-tagged CSN8 protein; lane 3—the cell extract after passing through the membrane; and lane 4—the eluate from the membrane.

Purification of His-Tagged HisU from Protein Mixtures:

To demonstrate the selectivity of PAA/PEI/PAA-Ni$^{2+}$-modified membranes for capture of His-tagged proteins, HisU was first separated from a mixture of HisU, Con A, BSA, Ovalbumin, and β-Lactoglobulin B. These model proteins, except HisU, do not have His-tags and serve as contaminating proteins in this experiment. SDS-PAGE analysis of the mixed-protein solution exiting the membrane suggests successful removal of HisU (FIG. 12(a) lane 3), while the eluate shows only bands due to HisU (FIG. 12(a) lane 4, note that even the as received HisU shows two bands). Thus, the membranes are highly selective for capturing HisU.

In addition to selectivity, high recovery is important in most protein purifications. The high purity of the eluted HisU (as demonstrated by gel electrophoresis) allowed the use of a Bradford assay to demonstrate that recovery was 95±3%, even with the loading, washing, and elution steps.

Example 5: Isolation of His-CSN8 from a Cell Extract

Cell Culture: The CSN8 orf was obtained through the *Drosophila* Genomics Resource Center and sub-cloned into the his-SUMO modified pet28b vector (Novagen). The plasmid was transformed into BL21DE3 codon plus (Stratagene) competent cells. Colonies were grown in LB broth (with Kanamycin and Chloramphenicol) at 37° C. until an O.D. of 0.8 was reached. The growth was induced with 0.4 mM isopropyl-thio-2-D-galactopyranoside (IPTG) for 16 hours at 16° C. The growth was pelleted by centrifugation. The pellet was resuspended in denaturing buffer containing 6 M urea, 10 mM Tris-HCl, and 100 mM NaH$_2$PO$_4$, at a pH of 8.0. The lysate was sonicated and then centrifuged to pellet the debris. The resulting supernatant was diluted 4:1 with 20 mM pH 8 phosphate buffer containing 10 mM imidazole, 300 mM NaCl, and 10% glycerol and stored in a −80° C. freezer until use.

Protein Isolation from a Cell Extract:

At a flow rate of 1.5 mL/min, the diluted lysate supernatant described above was passed through a PAA/PEI/PAA-NTA-Ni$^{2+}$-modified membrane that was equilibrated with lysate buffer (20 mM pH 8 phosphate buffer containing 10 mM imidazole and 300 mM NaCl). After washing with 20 mL washing buffer B, 20 mL washing buffer C (20 mM phosphate buffer containing 45 mM imidazole and 150 mM NaCl), and 20 mL phosphate buffer at a flow rate of 5 mL/min, protein elution and gel electrophoresis followed the same procedure for HisU purification.

Purification of His-Tagged CSN8 from Cell Extracts:

Purification of His-tagged CSN8 from whole cell extracts further demonstrates the high selectivity and potential applications of membranes modified with PAA/PEI/PAA-Ni$^{2+}$. FIG. 5(b) shows the SDS-PAGE analysis of the cell extract (lane 2) and the eluate from a membrane that was loaded with the cell extract and washed with buffers (lane 4). Remarkably, the eluate contains only one strong band, suggesting that the purity of the captured CSN8 is above 95%. Moreover, the complete membrane purification process requires less than 20 minutes, including loading cell lysate on the membrane, washing with 3 different buffers, and eluting.

Conclusions:

At pH 3, adsorption of as little as one layer of PAA in a porous membrane creates a high density of —COOH groups that function as either ion-exchange sites or points for attachment of metal-ion complexes that selectively bind proteins. Increasing the adsorption pH leads to much less protein binding, whereas adsorption of a PEI/PAA bilayer on the initial PAA layer increases lysozyme binding from 89 to 120 mg/cm$^3$ of membrane. Polyelectrolyte adsorption at low pH is much simpler than growth of polymer brushes in membranes, and the binding capacities that result from the two modification methods are similar. Derivatization of PAA/PEI/PAA-modified membranes with NTA-Ni$^{2+}$ complexes yields materials that selectively capture His-tagged protein with >90% recovery.

Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

SELECTED FIGURE ELEMENTS

- 100 porous membrane
- 104 functionalized porous membrane (including free acid groups)
- 108 functionalized porous membrane (including protein affinity tag-binding ligands)
- 110 substrate
- 115 pores
- 120 aqueous fluid mixture comprising a polyacid polymer
- 122 aqueous fluid mixture comprising a polyacid polymer with metal binding ligand groups
- 130 aqueous fluid mixture comprising a polyelectrolyte (adhesion promoter)
- 140 derivatization components
- 150 sample feed fluid including a positively charged analyte (A$^+$)
- 152 permeate fluid
- 154 elution/wash fluid
- 156 eluate fluid including positively charged analyte (A$^+$)
- 160 sample feed fluid including a protein analyte (P)
- 162 permeate fluid
- 164 elution/wash fluid
- 166 eluate (purified permeate) fluid including protein analyte (P)
- 200 polyacid layer
- 210 free acid groups (F)

212 analyte-bound free acid groups (FA$^+$)
220 protein affinity tag-binding ligands (L$_T$)
222 protein-bound ligands (L$_T$P)
300 adhesion/polyelectrolyte layer

REFERENCES (1) Clarke, W.; Hage, D. S. *Sep. Pur. Rev.* 2003, 32, 19-60.
(2) Kawai, T.; Saito, K.; Lee, W. *J. Chromatogr. B* 2003, 790, 131-142.
(3) Bhut, B. V.; Husson, S. M. *J. Membr. Sci.* 2009, 337, 215-223.
(4) Ghosh, R. *J. Chromatogr. A* 2002, 952, 13-27.
(5) Datta, S.; Bhattacharyya, D.; Ray, P. D.; Nath, A.; Toborek, M. *Sep. Sci. Technol.* 2007, 42, 2451-2471.
(6) Brandt, S.; Goffe, R. A.; Kessler, S. B.; O'Connor, J. L.; Zale, S. E. *Nat. Biotechnol.* 1988, 6, 779-782.
(7) Thömmes, J.; Etzel, M. *Biotechnol. Prog.* 2007, 23, 42-45.
(8) Roper, D. K.; Lightfoot, E. N. *J. Chromatogr. A* 1995, 702, 3-26.
(9) Lightfoot, E. N.; Moscariello, J. S. *Biotechnol. Bioeng.* 2004, 87, 259-273.
(10) Thömmes, J.; Kula, M.-R. *Biotechnol. Prog.* 1995, 11, 357-367.
(11) Saxena, A.; Tripathi, B. P.; Kumar, M.; Shahi, V. K. *Adv. Colloid Interface Sci.* 2009, 145, 1-22.
(12) Zeng, X. F.; Ruckenstein, E. *Biotechnol. Prog.* 1999, 15, 1003-1019.
(13) Sun, L.; Dai, J.; Baker, G. L.; Bruening, M. L. *Chem. Mater.* 2006, 18, 4033-4039.
(14) Jain, P.; Baker, G. L.; Bruening, M. L. *Ann. Rev. Anal. Chem.* 2009, 2, 387-408.
(15) Jain, P.; Dai, J.; Baker, G. L.; Bruening, M. L. *Macromolecules* 2008, 41, 8413-8417.
(16) Bruening, M. L.; Dotzauer, D. M.; Jain, P.; Lu, 0.; Baker, G. L. *Langmuir* 2008, 24, 7663-673.
(17) Jain, P.; Sun, L.; Dai, J.; Baker, G. L.; Bruening, M. L. *Biomacromolecules* 2007, 8, 3102-3107.
(18) Jain, P.; Vyas, M. K.; Geiger, J. H.; Baker, G. L.; Bruening, M. L. *Biomacromolecules* 2010, 11, 1019-1026.
(19) Bhut, B. V.; Christensen, K. A.; Husson, S. M. *J. Chromatogr., A* 2010, 1217, 12.
(20) Ulbricht, M.; Yang, H. *Chem. Mater.* 2005, 17, 2622-2631.
(21) Bhut, B. V.; Wickramasinghe, S. R.; Husson, S. M. *J. Membr. Sci.* 2008, 325, 176-183.
(22) He, D. M.; Ulbricht, M. *J. Membr. Sci.* 2008, 315, 155-163.
(23) Dai, J.; Bao, Z.; Sun, L.; Hong, S. U.; Baker, G. L.; Bruening, M. L. *Langmuir* 2006, 22, 4274-4281.
(24) Liu, G.; Dotzauer, D. M.; Bruening, M. L. *J. Membr. Sci.* 2010, 354, 198-205.
(25) Datta, S.; Cecil, C.; Bhattacharyya, D. *Ind. Eng. Chem. Res.* 2008, 47, 4586-4597.
(26) Product information for Mustang S membrane available from Pall Corporation (www.pall.com).
(27) Secrist, K. E.; Nolte, A. J. *Macromolecules* 2011, 44, 2859-2865.
(28) Quinn, A.; Such, G. K.; Quinn, J. F.; Caruso, F. *Adv. Funct. Mater.* 2008, 18, 17-26.
(29) Choi, J.; Rubner, M. F. *Macromolecules* 2005, 38, 116-124.
(30) Dubas, S. T.; Schlenoff, J. B. *Macromolecules* 2001, 34, 3736-3740.
(31) Bieker, P.; Schoenhoff, M. *Macromolecules* 2010, 43, 5052-5059.
(32) Harris, J. J.; Bruening, M. L. *Langmuir* 2000, 16, 2006-2013.
(33) Mendelsohn, J. D.; Yang, S. Y.; Hiller, J. A.; Hochbaum, A. I.; Rubner, M. F. *Biomacromolecules* 2003, 4, 96-106.
(34) Salloum, D. S.; Schlenoff, J. B. *Biomacromolecules* 2004, 5, 1089-1096.
(35) Ma, Y.; Bhattacharjee, S.; Wijeratne, S.; Bruening, M. L.; Baker, G. L. *Langmuir*, submitted.
(36) Anuraj, N.; Bhattacharjee, S.; Geiger, J. H.; Baker, G. L.; Bruening, M. L. *J. Membr. Sci.* 2012, 389, 117-125.
(37) Mossessova, E.; Lima, C. D. *Mol. Cell.* 2000, 5, 865-876.
(38) Wang, T. C.; Rubner, M. F.; Cohen, R. E. *Langmuir* 2002, 18, 3370-3375.
(39) Yoo, D.; Shiratori, S. S.; Rubner, M. F. *Macromolecules* 1998, 31, 4309-4318.
(40) Shiratori, S. S.; Rubner, M. F. *Macromolecules* 2000, 33, 4213-4219.
(41) Lee, D.; Nolte, A. J.; Kunz, A. L.; Rubner, M. F.; Cohen, R. E. *J. Am. Chem. Soc.* 2006, 128, 8521-8529.
(42) Ito, Y.; Park, Y. S.; Imanishi, Y. *J. Am. Chem. Soc.* 1997, 119, 2739-2740.
(43) Ito, Y.; Inaba, M.; Chung, D. J.; Imanishi, Y. *Macromolecules* 1992, 25, 7313-7316.
(44) Bergers, J. J.; Vingerhoeds, M. H.; van Bloois, L.; Herron, J. N.; Janssen, L. H. M.; Fischer, M. J. E.; Crommelin, D. J. A. *Biochemistry* 1993, 32, 4641-4649.
(45) Xu, F. J.; Zhao, J. P.; Kang, E. T.; Neoh, K. G.; Li, J. *Langmuir* 2007, 23, 8585-8592.
(46) Hardman, K. D.; Wood, M. K.; Schiffer, M.; Edmundson, A. B.; Ainsworth, C. F. *Proc. Natl. Acad. Sci. USA.* 1971 68, 1393-1397.
(47) Product information for Ni-NTA comples available from Qiagen (www1.giagen.com).

What is claimed is:
1. A polyacid-coated porous membrane comprising:
(a) a porous membrane substrate comprising a plurality of membrane pores; and
(b) a polyacid layer adsorbed on surfaces of the membrane pores, the polyacid layer comprising a polyacid polymer comprising one or more of free acid carboxylic acid groups, free acid carboxylate groups, and protein affinity tag-binding ligands;
wherein:
the polyacid polymer comprises at least the protein affinity tag-binding ligands;
the polyacid layer was deposited from a fluid mixture having a pH value lower than 4; and
the polyacid-coated porous membrane has a free acid group content higher than that of an analogous polyacid-coated porous membrane in which the polyacid layer was deposited from a fluid mixture having a pH value of 4, but which has been otherwise prepared equivalently to the polyacid-coated porous membrane.
2. The polyacid-coated porous membrane of claim 1, wherein the polyacid layer is adsorbed on the surfaces of the membrane pores due to one or more of hydrophobic interactions, hydrogen bonding interactions, and ionic interactions.
3. The polyacid-coated porous membrane of claim 1, wherein the protein affinity tag-binding ligand comprises derivatized free acid groups of the polyacid polymer, the derivatized free acid groups comprising a metal-binding ligand and a metallic ion complexed with the metal-binding ligand in a metal-ligand complex.

4. The polyacid-coated porous membrane of claim 1, wherein the protein affinity tag-binding ligand comprises a metal-binding ligand in repeating units of the polyacid polymer and a metallic ion complexed with the metal-binding ligand in a metal-ligand complex.

5. The polyacid-coated porous membrane of claim 1, wherein the polyacid layer is adsorbed on the surfaces of the membrane pores due to one or more of hydrophobic interactions and hydrogen bonding interactions, and is substantially free of covalent attachments to the surfaces of the membrane pores.

6. The polyacid-coated porous membrane of claim 1, comprising a plurality polyacid layers adsorbed on surfaces of the membrane pores, each polyacid layer comprising a polyacid polymer comprising one or more of free acid carboxylic acid groups, free acid carboxylate groups, and protein affinity tag-binding ligands;
wherein:
the first polyacid layer in the plurality of polyacid layers is adsorbed directly on the surfaces of the membrane pores;
one or more further polyacid layers in the plurality of polyacid layers are adhered to adjacent polyacid layers via one or more intervening polycation layers; and
the polyacid layer that is exposed to membrane pore void volumes comprises a polyacid polymer comprising at least the protein affinity tag-binding ligand.

7. The polyacid-coated porous membrane of claim 6, wherein the polycation layer is selected from the group consisting of polyethyleneimine (PEI), poly(allyl amine) (PAH), and combinations thereof.

8. The polyacid-coated porous membrane of claim 1, wherein the polyacid polymer comprises polyacrylic acid (PAA).

9. The polyacid-coated porous membrane of claim 1, wherein the polyacid layer is immobilized on the porous membrane substrate via one or more adhesion layers, wherein at least one of the adhesion layers is adsorbed directly on the porous membrane substrate.

10. The polyacid-coated porous membrane of claim 9, wherein the adhesion layer comprises poly(styrene sulfonate) (PSS).

11. The polyacid-coated porous membrane of claim 1, wherein the polyacid polymer comprises at least one of the free acid carboxylic acid groups and the free acid carboxylate groups.

12. The polyacid-coated porous membrane of claim 1, wherein the polyacid polymer comprises the free acid carboxylic acid groups and the free acid carboxylate groups.

13. The polyacid-coated porous membrane of claim 1, wherein the protein affinity tag-binding ligand comprises metallic ions.

14. The polyacid-coated porous membrane of claim 13, wherein the metallic ions comprise $Ni^{2+}$.

15. The polyacid-coated porous membrane of claim 13, wherein the metallic ions comprise one or more of $Cu^{2+}$, $Co^{2+}$, $Fe^{3+}$, and $Ga^{3+}$.

16. The polyacid-coated porous membrane of claim 1, wherein the protein affinity tag-binding ligands are selected from the group consisting of glutathione, glutathione-S-transferase (GST) tag binding derivatives, amylose, maltose binding protein (MBP) tag binding derivatives thereof, chitin, chitin binding protein (CBP) tag-binding derivatives thereof, and combinations thereof.

17. The polyacid-coated porous membrane of claim 1, wherein the plurality of membrane pores has an average pore size ranging from 0.02 μm to 50 μm.

18. The polyacid-coated porous membrane of claim 1, wherein the plurality of membrane pores comprises pores having a size of about 0.5 μm.

19. The polyacid-coated porous membrane of claim 1, wherein the membrane has a protein binding capacity of at least about 90 mg protein/$cm^3$ of the membrane.

20. The polyacid-coated porous membrane of claim 1, wherein the membrane has a protein binding capacity of about 90 to 135 mg protein/$cm^3$ of the membrane.

21. The polyacid-coated porous membrane of claim 1, further comprising a target protein comprising an affinity tag, the target protein being bound via the affinity tag with the protein affinity tag-binding ligand of the membrane.

22. A polyacid-coated porous membrane comprising:
(a) a porous membrane substrate comprising a plurality of membrane pores; and
(b) a plurality of polyacid layers adsorbed on surfaces of the membrane pores, each polyacid layer comprising a polyacid polymer comprising free acid groups selected from the group consisting of carboxylic acid groups, carboxylate groups, and combinations thereof;
wherein:
the first polyacid layer in the plurality of polyacid layers is adsorbed directly on the surfaces of the membrane pores and is substantially free of covalent attachments to the surfaces of the membrane pores;
one or more further polyacid layers in the plurality of polyacid layers are adhered to adjacent polyacid layers via one or more intervening polycation layers;
the polyacid layers were deposited from a fluid mixture having a pH value lower than 4; and
the polyacid-coated porous membrane has a free acid group content higher than that of an analogous polyacid-coated porous membrane in which the polyacid layers were deposited from a fluid mixture having a pH value of 4, but which has been otherwise prepared equivalently to the polyacid-coated porous membrane.

23. A polyacid-coated porous membrane comprising:
(a) a porous membrane substrate comprising a plurality of membrane pores; and
(b) a polyacid layer adsorbed on surfaces of the membrane pores, the polyacid layer comprising a polyacid polymer comprising free acid groups selected from the group consisting of carboxylic acid groups, carboxylate groups, and combinations thereof;
wherein:
the polyacid layer is adsorbed on the surfaces of the membrane pores via one or more adhesion layers and is substantially free of covalent attachments to the surfaces of the membrane pores, wherein at least one of the adhesion layers is adsorbed directly on the porous membrane substrate;
the polyacid layer was deposited from a fluid mixture having a pH value lower than 4; and
the polyacid-coated porous membrane has a free acid group content higher than that of an analogous polyacid-coated porous membrane in which the polyacid layer was deposited from a fluid mixture having a pH value of 4, but which has been otherwise prepared equivalently to the polyacid-coated porous membrane.

24. The polyacid-coated porous membrane of claim 23, wherein the adhesion layer adsorbed directly on the porous membrane substrate comprises a polyelectrolyte other than the polyacid polymer.

25. The polyacid-coated porous membrane of claim 22, wherein the polyacid-coated porous membrane has a free acid group content ranging from 1.25 to 10 times that of an analogous polyacid-coated porous membrane.

26. The polyacid-coated porous membrane of claim 23, wherein the polyacid-coated porous membrane has a free acid group content ranging from 1.25 to 10 times that of an analogous polyacid-coated porous membrane.

27. The polyacid-coated porous membrane of claim 1, wherein the polyacid-coated porous membrane has a free acid group content ranging from 1.25 to 10 times that of an analogous polyacid-coated porous membrane.

28. A method for binding an affinity-tagged target protein, the method comprising:
  (a) providing the polyacid-coated porous membrane according to claim 1;
  (b) providing a feed fluid sample comprising a target protein comprising an affinity tag; and
  (c) passing the feed fluid sample through the polyacid-coated porous membrane, thereby (i) binding at least some of the target protein via the affinity tag with the immobilized protein affinity tag-binding ligands and (ii) providing a permeate fluid with at least some of the target protein removed.

29. The method of claim 28, wherein (i) the affinity tag is a polyhistidine tag and (ii) the protein affinity tag-binding ligands comprise one or more of $Ni^{2+}$-ligand complexes and $Co^{2+}$-ligand complexes.

30. The method of claim 28, wherein (i) the affinity tag is a glutathione-S-transferase (GST) tag and (ii) the protein affinity tag-binding ligands are selected from the group consisting of glutathione, glutathione-S-transferase (GST) tag-binding derivatives thereof, and combinations thereof.

31. The method of claim 28, wherein (i) the affinity tag is a maltose binding protein (MBP) tag and (ii) the protein affinity tag-binding ligands are selected from the group consisting of amylose, maltose binding protein (MBP) tag-binding derivatives thereof, and combinations thereof.

32. The method of claim 28, wherein (i) the affinity tag is chitin binding protein (CBP) tag and (ii) the protein affinity tag-binding ligands are selected from the group consisting of chitin, chitin binding protein (CBP) tag-binding derivatives thereof, and combinations thereof.

33. The method of claim 28, further comprising:
  (d) eluting the bound target protein from the polyacid-coated porous membrane, thereby forming a purified permeate comprising the target protein.

34. The method of claim 33, wherein (i) the feed fluid sample further comprises non-target proteins and (ii) the purified permeate is substantially free from the non-target proteins.

* * * * *